United States Patent
Roe et al.

(10) Patent No.: US 8,569,568 B2
(45) Date of Patent: *Oct. 29, 2013

(54) ARTICLE HAVING IMPROVED FECAL STORAGE STRUCTURE

(75) Inventors: Donald Carroll Roe, West Chester, OH (US); Cheryl D. Fox, Cincinnati, OH (US); Aleksey M. Pinyayev, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 344 days.

This patent is subject to a terminal disclaimer.

(21) Appl. No.: 13/070,806

(22) Filed: Mar. 24, 2011

(65) Prior Publication Data

US 2011/0172623 A1      Jul. 14, 2011

Related U.S. Application Data

(60) Division of application No. 10/757,813, filed on Jan. 15, 2004, now Pat. No. 7,935,859, which is a continuation of application No. 09/172,405, filed on Oct. 14, 1998, now Pat. No. 6,703,537.

(60) Provisional application No. 60/066,777, filed on Nov. 14, 1997.

(51) Int. Cl.
*A61F 13/15* (2006.01)
*A61F 13/20* (2006.01)

(52) U.S. Cl.
USPC .................................... 604/367; 604/385.01

(58) Field of Classification Search
USPC .............. 604/367–369, 374, 378, 383–384, 604/385.01
See application file for complete search history.

(56) References Cited

U.S. PATENT DOCUMENTS

| | | | |
|---|---|---|---|
| 2,696,618 A | 7/1959 | Schaefer |
| 3,284,273 A | 11/1966 | Prentice |
| 3,371,667 A | 3/1968 | Morse |
| 3,489,148 A | 1/1970 | Duncan et al. |
| 3,491,759 A | 1/1970 | Samuel |
| 3,532,097 A | 10/1970 | Jones, Sr. |
| 3,585,998 A | 6/1971 | Hayford |
| 3,593,717 A | 7/1971 | Jones, Sr. |
| 3,759,262 A | 9/1973 | Jones, Sr. |
| 3,846,594 A | 11/1974 | Buell |
| 3,860,003 A | 1/1975 | Buell |
| 3,875,942 A | 4/1975 | Roberts et al. |
| 3,890,973 A | 6/1975 | Davis et al. |
| 3,896,807 A | 7/1975 | Buchalter |
| 3,911,173 A | 10/1975 | Sprague, Jr. |

(Continued)

FOREIGN PATENT DOCUMENTS

| | | |
|---|---|---|
| CA | 2049398 | 2/1992 |
| DE | 3 301 555 A1 | 8/1984 |

(Continued)

*Primary Examiner* — Michele M Kidwell
(74) *Attorney, Agent, or Firm* — Andrew J. Mueller; Laura L. Whitmer

(57) ABSTRACT

An absorbent article comprising a liquid pervious topsheet, a liquid pervious backsheet joined to at least a portion of the topsheet, an absorbent core disposed between at least a portion of the topsheet and the backsheet, and a waste management element disposed in at least a portion of the crotch region. The waste management element preferably includes an acceptance element having an effective open area of at least about 30 percent and a storage element having a compressive resistance of at least about 70 percent.

15 Claims, 20 Drawing Sheets

(56) References Cited

U.S. PATENT DOCUMENTS

| | | |
|---|---|---|
| 3,929,135 A | 12/1975 | Thompson |
| 3,945,386 A | 3/1976 | Anczurowski et al. |
| 3,964,486 A | 6/1976 | Blaney |
| 3,967,623 A | 7/1976 | Butterworth et al. |
| 4,027,672 A | 6/1977 | Karami |
| 4,047,531 A | 9/1977 | Karami |
| 4,055,180 A | 10/1977 | Karami |
| 4,173,042 A | 11/1979 | Krzewinski-Morris |
| 4,321,924 A | 3/1982 | Ahr |
| 4,324,246 A | 4/1982 | Mullane et al. |
| 4,324,247 A | 4/1982 | Aziz |
| 4,342,314 A | 8/1982 | Radel et al. |
| 4,360,021 A | 11/1982 | Stima |
| 4,381,781 A | 5/1983 | Sciaraffa et al. |
| 4,381,782 A | 5/1983 | Mazurak et al. |
| 4,385,632 A | 5/1983 | Odelhog |
| 4,392,861 A | 7/1983 | Butterworth et al. |
| 4,397,644 A | 8/1983 | Matthews et al. |
| 4,401,712 A | 8/1983 | Morrison |
| 4,463,045 A | 7/1984 | Ahr et al. |
| 4,501,586 A | 2/1985 | Holtman |
| 4,515,595 A | 5/1985 | Kievit et al. |
| 4,556,560 A | 12/1985 | Buckingham |
| 4,573,986 A | 3/1986 | Minetola et al. |
| 4,609,518 A | 9/1986 | Curro et al. |
| 4,610,678 A | 9/1986 | Weisman et al. |
| 4,613,447 A | 9/1986 | Hara et al. |
| 4,622,036 A | 11/1986 | Goodrum |
| 4,623,339 A | 11/1986 | Ciraldo et al. |
| 4,629,643 A | 12/1986 | Curro et al. |
| 4,643,727 A | 2/1987 | Rosenbaum |
| 4,657,537 A | 4/1987 | Zimmerer |
| 4,662,875 A | 5/1987 | Hirotsu et al. |
| 4,662,877 A | 5/1987 | Williams |
| 4,673,402 A | 6/1987 | Weisman et al. |
| 4,676,785 A | 6/1987 | Battista |
| 4,678,464 A | 7/1987 | Holtman |
| 4,685,909 A | 8/1987 | Berg et al. |
| 4,695,278 A | 9/1987 | Lawson |
| 4,699,823 A | 10/1987 | Kellenberger et al. |
| 4,704,112 A | 11/1987 | Suzuki et al. |
| 4,710,189 A | 12/1987 | Lash |
| 4,723,953 A | 2/1988 | Rosenbaum et al. |
| 4,785,996 A | 11/1988 | Zlecker et al. |
| 4,790,836 A | 12/1988 | Brecher |
| 4,795,454 A | 1/1989 | Dragoo |
| 4,798,603 A | 1/1989 | Meyer et al. |
| 4,804,378 A | 2/1989 | Shiba et al. |
| 4,808,178 A | 2/1989 | Aziz et al. |
| 4,816,025 A | 3/1989 | Foreman |
| 4,834,735 A | 5/1989 | Alemany et al. |
| 4,842,593 A | 6/1989 | Jordan et al. |
| 4,842,666 A | 6/1989 | Werenicz |
| 4,846,815 A | 7/1989 | Scripps |
| 4,857,067 A | 8/1989 | Wood et al. |
| 4,885,204 A | 12/1989 | Bither et al. |
| 4,888,231 A | 12/1989 | Angstadt |
| 4,892,528 A | 1/1990 | Suzuki et al. |
| 4,892,536 A | 1/1990 | DesMarais et al. |
| 4,894,060 A | 1/1990 | Nestegard |
| 4,898,642 A | 2/1990 | Moore et al. |
| 4,908,026 A | 3/1990 | Sukiennik et al. |
| 4,909,803 A | 3/1990 | Aziz et al. |
| 4,935,022 A | 6/1990 | Lash et al. |
| 4,938,753 A | 7/1990 | Van Gompel et al. |
| 4,946,527 A | 8/1990 | Battrell |
| 4,963,140 A | 10/1990 | Robertson et al. |
| 4,968,312 A | 11/1990 | Khan |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,026,364 A | 6/1991 | Robertson |
| 5,037,409 A | 8/1991 | Chen et al. |
| 5,037,416 A | 8/1991 | Allen et al. |
| 5,062,840 A | 11/1991 | Holt et al. |
| 5,071,681 A | 12/1991 | Manning et al. |
| 5,098,764 A | 3/1992 | Drelich et al. |
| 5,124,197 A | 6/1992 | Bernardin et al. |
| 5,134,007 A | 7/1992 | Reising et al. |
| 5,135,521 A | 8/1992 | Luceri et al. |
| 5,137,537 A | 8/1992 | Herron et al. |
| 5,143,779 A | 9/1992 | Newkirk et al. |
| 5,147,343 A | 9/1992 | Kellenberger |
| 5,147,345 A | 9/1992 | Young et al. |
| 5,149,335 A | 9/1992 | Kellenberger et al. |
| 5,151,092 A | 9/1992 | Buell et al. |
| 5,171,236 A | 12/1992 | Dreier et al. |
| 5,171,238 A | 12/1992 | Kajander |
| 5,176,672 A | 1/1993 | Bruemmer et al. |
| 5,192,277 A | 3/1993 | Chung et al. |
| 5,192,606 A | 3/1993 | Proxmire et al. |
| 5,204,158 A | 4/1993 | Phillips et al. |
| 5,207,663 A | 5/1993 | McQueen |
| 5,221,274 A | 6/1993 | Buell et al. |
| 5,244,711 A | 9/1993 | Drelich et al. |
| 5,260,345 A | 11/1993 | DesMarais et al. |
| 5,269,775 A | 12/1993 | Freeland et al. |
| 5,281,208 A | 1/1994 | Thompson et al. |
| 5,304,159 A | 4/1994 | Tanji et al. |
| 5,304,160 A | 4/1994 | Igaue et al. |
| 5,306,266 A | 4/1994 | Freeland |
| 5,330,459 A | 7/1994 | Lavon et al. |
| 5,342,338 A | 8/1994 | Roe |
| 5,342,342 A | 8/1994 | Kitaoka |
| 5,344,516 A | 9/1994 | Tanji et al. |
| 5,352,217 A | 10/1994 | Curro |
| 5,356,405 A | 10/1994 | Thompson et al. |
| 5,387,207 A | 2/1995 | Dyer et al. |
| 5,387,209 A | 2/1995 | Yamamoto et al. |
| 5,397,318 A | 3/1995 | Dreier |
| 5,429,632 A | 7/1995 | Tanji et al. |
| 5,439,458 A | 8/1995 | Noel et al. |
| 5,439,459 A | 8/1995 | Tanji et al. |
| 5,462,541 A | 10/1995 | Bruemmer et al. |
| 5,468,236 A | 11/1995 | Everhart et al. |
| 5,514,121 A | 5/1996 | Roe et al. |
| 5,518,801 A | 5/1996 | Chappell et al. |
| 5,520,674 A | 5/1996 | Lavon et al. |
| 5,525,346 A | 6/1996 | Hartung et al. |
| 5,540,671 A | 7/1996 | Dreier |
| 5,545,155 A | 8/1996 | Hseih et al. |
| 5,554,142 A | 9/1996 | Dreier et al. |
| 5,569,234 A | 10/1996 | Buell et al. |
| 5,571,096 A | 11/1996 | Dobrin et al. |
| 5,579,722 A | 12/1996 | Yamamoto et al. |
| 5,580,411 A | 12/1996 | Nease et al. |
| 5,586,978 A | 12/1996 | Bayne |
| 5,603,707 A | 2/1997 | Trombetta et al. |
| 5,607,760 A | 3/1997 | Roe |
| 5,609,587 A | 3/1997 | Roe |
| 5,628,097 A | 5/1997 | Benson et al. |
| 5,635,191 A | 6/1997 | Roe et al. |
| H1670 H | 7/1997 | Aziz et al. |
| 5,643,588 A | 7/1997 | Roe et al. |
| 5,650,222 A | 7/1997 | DesMarais |
| 5,653,703 A | 8/1997 | Roe et al. |
| 5,669,897 A | 9/1997 | Lavon et al. |
| 5,674,213 A | 10/1997 | Sauer |
| 5,676,661 A | 10/1997 | Faulks et al. |
| 5,776,122 A | 7/1998 | Faulks et al. |
| 5,779,690 A | 7/1998 | Gustafsson et al. |
| 5,810,798 A | 9/1998 | Finch et al. |
| 5,824,172 A | 10/1998 | Kielpikowski |
| 5,830,203 A | 11/1998 | Suzuki et al. |
| 5,865,823 A | 2/1999 | Curro |
| 5,925,026 A | 7/1999 | Arteman et al. |
| 5,938,650 A | 8/1999 | Baer et al. |
| 5,941,863 A | 8/1999 | Guidotti et al. |
| 5,957,906 A | 9/1999 | Roe et al. |
| 5,976,665 A | 11/1999 | Hansson |
| 6,004,306 A | 12/1999 | Robles et al. |

(56) References Cited

U.S. PATENT DOCUMENTS

| | | | |
|---|---|---|---|
| 6,010,491 | A | 1/2000 | Roe et al. |
| 6,703,537 | B1 | 3/2004 | Roe et al. |
| 2004/0147889 | A1 | 7/2004 | Roe et al. |

FOREIGN PATENT DOCUMENTS

| | | |
|---|---|---|
| DE | 4138540 | 5/1992 |
| EP | 0 355 740 A2 | 2/1980 |
| EP | 0 160 569 A2 | 11/1985 |
| EP | 0 160 572 A2 | 11/1985 |
| EP | 0 193 309 A1 | 9/1986 |
| EP | 0 215 417 A1 | 3/1987 |
| EP | 0 418 493 A1 | 3/1991 |
| EP | 0 470 392 A1 | 2/1992 |
| EP | 0 495 212 A1 | 7/1992 |
| EP | 0 059 498 A1 | 9/1992 |
| EP | 0 545 423 A1 | 6/1993 |
| EP | 0 581 044 | 2/1994 |
| EP | 0 626 161 | 11/1994 |
| EP | 0 359 501 B1 | 12/1994 |
| EP | 0 745 367 | 12/1996 |
| EP | 0 758 543 | 2/1997 |
| EP | 0815819 A2 | 1/1998 |
| EP | 0826349 A2 | 3/1998 |
| EP | 0 847 738 | 6/1998 |
| EP | 0 933 074 | 8/1999 |
| ES | 2022026 | 11/1991 |
| FR | 2504799 | 11/1982 |
| FR | 2561078 | 9/1985 |
| GB | 2103933 A | 3/1983 |
| GB | 2 255 720 A | 11/1992 |
| GB | 2268073 | 1/1994 |
| JP | 2-31756 | 2/1990 |
| JP | 4-152945 | 10/1990 |
| JP | 5-49659 | 8/1991 |
| JP | 3-202057 | 9/1991 |
| JP | 4221556 | 8/1992 |
| JP | 4-263857 | 9/1992 |
| JP | 5-86320 | 11/1993 |
| JP | 6-17726 | 3/1994 |
| JP | 6-31723 | 4/1994 |
| JP | 6-34618 | 5/1994 |
| JP | 6-038818 | 5/1994 |
| JP | 6-74132 | 10/1994 |
| JP | 6-102070 | 12/1994 |
| JP | 7-7620 | 2/1995 |
| JP | 8-117261 | 5/1996 |
| JP | 8-181857 | 7/1996 |
| JP | 2565491 | 10/1996 |
| JP | 2565492 | 10/1996 |
| JP | 2565493 | 10/1996 |
| JP | 2518012 | 11/1996 |
| JP | 9-51911 | 2/1997 |
| JP | 2547103 | 5/1997 |
| JP | 9-141091 | 6/1997 |
| JP | 9-238979 | 8/1997 |
| JP | 255948 | 9/1997 |
| JP | 2559752 | 9/1997 |
| JP | 9-276333 | 10/1997 |
| JP | 10-14978 | 1/1998 |
| JP | 10-14979 | 1/1998 |
| JP | 10-165436 | 6/1998 |
| JP | 10-192339 | 7/1998 |
| JP | 10-234760 | 9/1998 |
| JP | 10-234775 | 9/1998 |
| WO | WO 89/11843 A1 | 12/1989 |
| WO | WO 91/09582 A1 | 7/1991 |
| WO | WO 91/10415 A1 | 7/1991 |
| WO | WO 92/18078 A1 | 10/1992 |
| WO | WO 93/03699 A2 | 3/1993 |
| WO | WO 93/09741 | 5/1993 |
| WO | WO 93/09744 | 5/1993 |
| WO | WO 93/25172 | 12/1993 |
| WO | WO 94/14395 | 7/1994 |
| WO | WO 95/16417 | 6/1995 |
| WO | WO 95/16418 | 6/1995 |
| WO | WO 95/16422 | 6/1995 |
| WO | WO 95/16746 | 6/1995 |
| WO | WO 95/24173 | 9/1995 |
| WO | WO 95/25493 | 9/1995 |
| WO | WO 96/09026 | 3/1996 |
| WO | WO 96/19167 | 6/1996 |
| WO | WO 96/23466 | 8/1996 |
| WO | WO 96/23467 | 8/1996 |
| WO | WO 96/40029 | 12/1996 |
| WO | WO 97/01316 | 1/1997 |
| WO | WO 97/02846 | 1/1997 |
| WO | WO 97/14368 | 4/1997 |
| WO | WO 97/14385 | 4/1997 |
| WO | WO 97/16144 | 5/1997 |
| WO | WO 97/21409 | 6/1997 |
| WO | WO 97/22319 | 6/1997 |
| WO | WO 97/49366 | 12/1997 |
| WO | WO 98/08476 | 3/1998 |
| WO | WO 98/16179 | 4/1998 |
| WO | WO 98/16180 | 4/1998 |
| WO | WO 98/17219 | 4/1998 |
| WO | WO 98/27907 | 7/1998 |
| WO | WO 98/37838 | 9/1998 |
| WO | WO 98/37839 | 9/1998 |
| WO | WO 98/37844 | 9/1998 |
| WO | WO 99/30661 | 6/1999 |

ARTICLE HAVING IMPROVED FECAL STORAGE STRUCTURE

CROSS REFERENCE TO RELATED APPLICATION

This application is a divisional of application U.S. Ser. No. 10/757,813, filed Jan. 15, 2004, now U.S. Pat. No. 7,935,859 which is a continuation of U.S. Ser. No. 09/172,405, filed Oct. 14, 1998, now U.S. Pat. No. 6,703,537 which claimed the benefit of U.S. Provisional Application 60/066,777, filed Nov. 14, 1997.

FIELD OF THE INVENTION

The present invention relates to articles which absorb and/or contain bodily exudates, including disposable absorbent articles such as diapers, adult incontinence products, sanitary napkins and the like. More particularly, the invention relates to disposable absorbent articles having improved fecal material management properties.

BACKGROUND OF THE INVENTION

The major function of absorbent articles such as diapers and adult incontinence briefs is to prevent body exudates from soiling, wetting, or otherwise contaminating clothing or other articles, such as bedding, that come in contact with the wearer. In recent years, disposable diapers such as those disclosed in U.S. Pat. No. 3,860,003 issued to Kenneth Barclay Buell on Jan. 14, 1975 have become very popular with the public and have generally replaced durable cloth absorbent articles because of their convenience and reliability. However, despite the effectiveness of such disposable absorbent articles, body exudates often still leak or are stored in the diaper such that the exudates soil and/or irritate the skin of the wearer.

The undesirable effects of leakage and/or improper containment are especially evident with regard to fecal matter deposited in the diaper. Feces contained in the diaper can harm the skin of the wearer over time, and feces, leaking from the diaper, almost invariably presents unpleasant messy clean-ups. Thus, several attempts have been made to add features to diapers such as barriers, pockets, spacers, transverse barriers, apertured topsheets and the like to limit the movement of the material across the topsheet and/or to better confine fecal matter in the diaper. However, such attempts have been generally unsuccessful due to their cost and complexity or due to their limited success in reducing the negative effects of the feces.

Although the present invention may be adapted to provide improved management of any bodily exudates, the embodiments described hereinbelow are especially suitable for controlling viscous fluid bodily wastes. Such viscous fluid bodily wastes include soft or runny feces, and the like, which are generally more viscous than urine but less viscous than normal solid adult feces. Viscous fluid bodily wastes are difficult to absorb and/or contain in conventional absorbent structures because the normal capillary forces which acquire and transport extremely low viscosity fluids like urine are insufficient to move such viscous fluid bodily wastes. Thus, the viscous fluid body wastes often remain on the topsheet of the article where they are generally unrestricted in movement and accessible to and in contact with the wearer's skin. Further, the fluid characteristics of the waste permit it to flow across the topsheet and sometimes leak out of the article. Accordingly, the special characteristics of viscous fluid bodily wastes need to be addressed by unique storage structures.

Accordingly, it would be desirable to provide an absorbent structure with improved feces management properties. Further, it would be advantageous to provide an economical disposable absorbent article with the ability to minimize the negative effects of feces or other viscous fluid bodily waste on the wearer or the caregiver. It would also be advantageous to provide an absorbent article which is specifically designed to accept viscous fluid bodily wastes such as fecal material, especially relatively lower viscosity fecal material such as soft or runny feces. Also, it would be desirable to provide an absorbent article having sufficient effective capacity and retention capability to store feces deposited therein safely and cleanly away from the wearer's skin and/or clothing throughout the expected time of use.

SUMMARY OF THE INVENTION

In order to better manage viscous fluid bodily wastes, the present invention provides an absorbent article having a first waist region, a second waist region opposed to the first waist region and a crotch region disposed between the first waist region and the second waist region. The absorbent article comprises a liquid pervious topsheet, a liquid impervious backsheet joined to at least a portion of the topsheet, an absorbent core disposed between at least a portion of the topsheet and the backsheet, and a waste management element disposed in at least a portion of the crotch region. The waste management element includes an acceptance element having an effective open area of at least about 30% and an Acceptance Under Pressure value of greater than about 0.70 grams of a viscous fluid bodily waste per square inch of the acceptance element per millijoule of energy input. The waste management element further includes a storage element disposed between at least a portion of the acceptance element and the backsheet. The storage element has a compressive resistance of at least about 70% and a Storage Under Pressure value of greater than about 0.70 grams of the viscous fluid bodily waste per square inch of the storage element. The effective open area ensures that viscous fluid bodily wastes are quickly and efficiently imbibed by the article. Further, the improved compressive resistance may reduce the likelihood that normal wearing forces will release the waste from the storage element once the waste is imbibed by the article. Accordingly, the absorbent article of the present invention may reduce the likelihood of harm to the wearer's skin and/or the inconvenience to the caregiver normally associated with bowel movements, and especially runny feces.

BRIEF DESCRIPTION OF THE DRAWINGS

While the specification concludes with claims particularly pointing out and distinctly claiming the subject matter which is regarded as the present invention, it is believed that the description will be better understood from the following descriptions which are taken in conjunction with the accompanying drawings in which like designations are used to designate substantially identical elements.

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, wipes, mops, bandages and the like.

Figure 1:
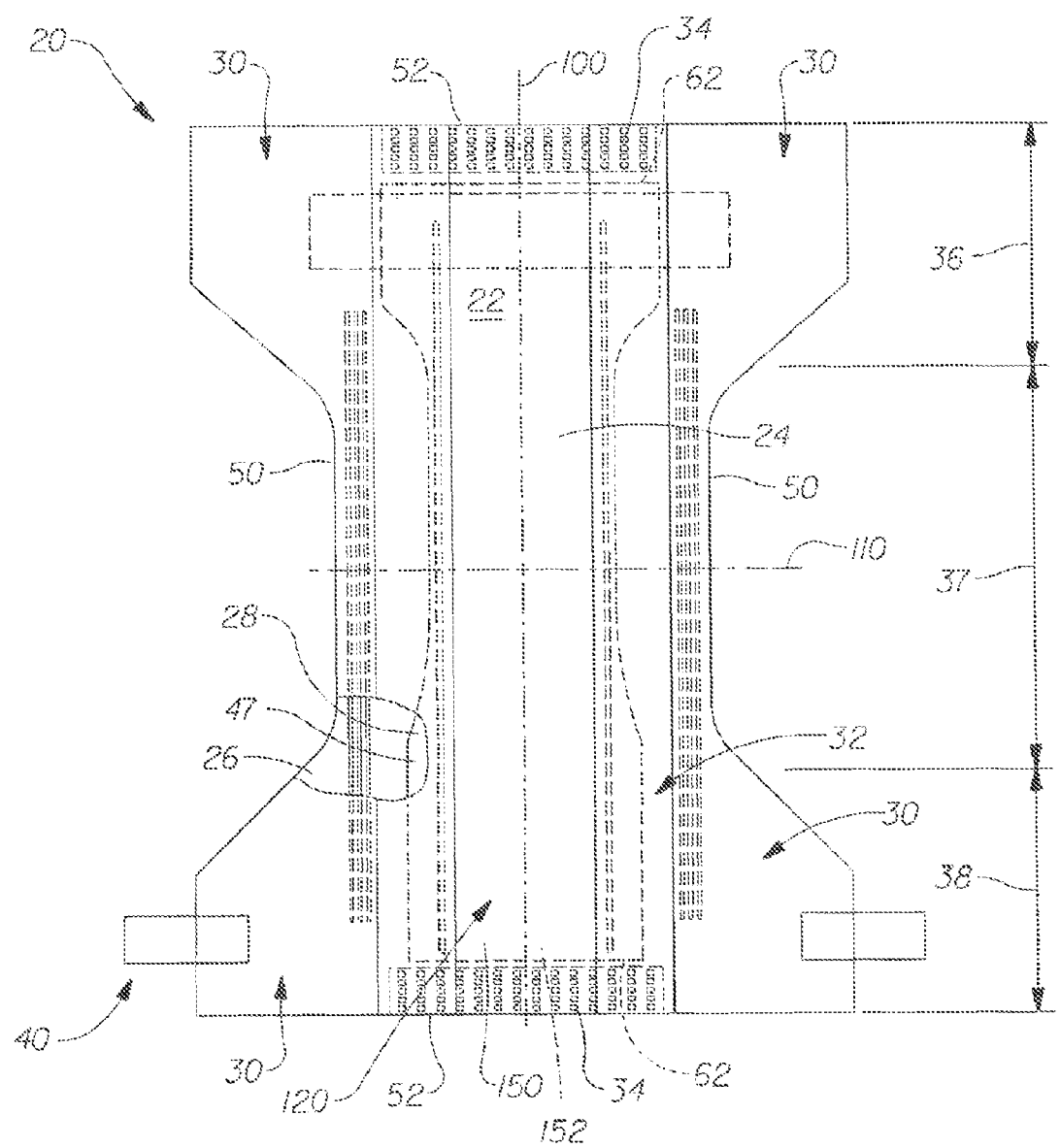
FIG. 1 is a plan view of an absorbent article embodiment of the present invention having portions cut away to reveal the underlying structure, the body-facing surface of the diaper facing the viewer.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 40. Diaper 20 is shown in FIG. 1 to have a first waist region 36, a second waist region 38 opposed to the first waist region 36 and a crotch region 37 located between the first waist region and the second waist region. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/915,471 entitled "Absorbent Article With Multi-Directional Extensible Side Panels" filed Aug. 20, 1997 in the name of Robles et al.; each of which is incorporated herein by reference.

The backsheet 26 is generally that portion of the diaper 20 positioned adjacent the garment facing surface of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mils) to about 0.051 mm (2.0 mils). Suitable backsheet films include those manufactured by Tredegar Industries Inc. of Terre Haute, Ind. and sold under the trade name CPC2 FILM. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by Tredegar Corp. of Richmond, Va. under the designation EXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E.I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials. The SELF web includes a stainable network having at least two contiguous, distinct, and dissimilar regions. Preferably, one of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Adhesives which have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent the body surface 47 of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to other elements of the diaper 20.

The topsheet 24 is preferably compliant, soft feeling, and non-irritating to the wearer's skin. Further, at least a portion of the topsheet 24 is liquid pervious, permitting liquids to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the absorbent assemblies include fibers, the fibers may be spunbond, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets 30 are made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Procter & Gamble Company of Cincinnati, Ohio as DRI-WEAVE and from Tredegar Corporation of Terre Haute, Ind. as CLIFF-T.

Preferably, the topsheet 24 is made of a hydrophobic material or is treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating surfactant in the topsheet can be found in U.S. Statutory Invention Registration No. H1670, published on Jul. 1, 1997 in the names of Aziz et al. Each of these references is hereby incorporated by reference herein. Alternatively, the topsheet 24 may include an apertured web or film which is hydrophobic. This may be accomplished eliminating the hydrophilizing treatment step from the production process and/or applying a hydrophobic treatment to the topsheet 24, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotion Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysiloxane Emollient" which issued to Roe et al. on Jun. 3, 1997; and U.S. Pat. No. 5,643,588 entitled "Diaper Having A Lotioned Topsheet" which issued to Roe et al. on Jul. 1, 1997. The lotion may function alone or in combination with another agent as the hydrophobizing treatment described above. The topsheet may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished to provide a more cloth like appearance.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including conform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the diaper 20.

Exemplary absorbent structures for use as the absorbent assemblies are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,650,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The diaper 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge 62 of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 20 may also include a fastening system 40. The fastening system 40 preferably maintains the first waist region 36 and the second waist region 38 in an overlapping configuration so as to provide lateral tensions about the circumference of the diaper 20 to hold the diaper 20 on the wearer. The fastening system 40 preferably comprises tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151,092 issued to Buell on Sep. 9, 1992; and U.S. Pat. No. 5,221,274 issued to Buell on Jun. 22, 1993. The fastening system may also provide a means for holding the article in a disposal configuration as disclosed in U.S. Pat. No. 4,963,140 issued to Robertson et al. on Oct. 16, 1990. Each of these patents is incorporated herein by reference. In alternative embodiments, opposing sides of the garment may be seamed or welded to form a pant. This allows the article to be used as a pull-on type diaper, such as a training pant.

The diaper 20 may also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the diaper pulls one elasticized side panel 30 farther than the other during application, the diaper 20 will "self-adjust" during wear.

While the diaper 20 of the present invention preferably has the side panels 30 disposed in the second waist region 38, the diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/155,048 entitled "Absorbent Article With Multi-Directional Extensible Side Panels" filed Nov. 19, 1993 in the names of Robles, et al.; each of which is incorporated herein by reference.

The diaper 20 preferably further includes leg cuffs 32 which provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,062,840, entitled "Disposable Diapers", issued to Holt et al on Nov. 5, 1991; and U.S. Pat. No. 5,269,775 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition, issued Aug. 5, 1997 to Roe, et al. All of the above-cited references are hereby incorporated by reference herein.

In addition to or in place of the voids, pockets and barriers, described above, embodiments of the present invention preferably include a waste management element 120 capable of effectively and efficiently accepting, storing and/or immobilizing viscous fluid bodily waste, such as runny feces or menses. The waste management element 120 can be located anywhere in the article, including the crotch region or either waist region, or may be associated with or be included in any structure or element such as the core 28, a leg cuff, etc. In preferred embodiments, the waste management element 120 is located in the region of the article that is near the wearer's perianal region when worn. This helps ensure that any waste discharged is deposited on or near the waste management element 120.

As used herein, the term "viscous fluid bodily waste" or "VFBW" generally refers to any waste discarded from the body which has a viscosity of greater than about 10 cP and less than about $2 \times 10^5$ cP at a shear rate of one 1/sec, (at about 35 degrees C.), more particularly between about $10^3$ cP and $10^5$ cP at a one 1/sec shear rate, in a controlled stress rheometry test using parallel plates on a controlled stress rheometer. (For reference, water is at 1.0 cP at 20 degrees C. and Jif Creamy peanut butter (available from the Procter & Gamble Co., Cincinnati, Ohio) is approximately $4 \times 10^5$ cP at 25 degrees C. at this same shear rate). The method for determining viscosity, as used herein, is described in detail in the Test Method section below.

As used herein, the term "accept" or "acceptance" refers to the penetration of a structure by materials deposited thereon. Specifically, the term accept refers to the penetration of a structure by a fluid when subjected to the conditions set forth in the Acceptance Under Pressure Test, described in the Test Methods Section. Penetration is defined by the passage of materials through the surface of the structure upon which the material was deposited. Penetration of nonuniform structures can be defined as the passage of a material through a plane defining the surface upon which the material was deposited. Acceptance Under Pressure, or "acceptance" is measured as the amount of material that penetrates the surface of the structure per unit area per unit work done. "Work" is an energy term referring to the application of force through a distance. Thus, structures or elements that more readily accept viscous fluid bodily wastes require less energy to be expended per unit mass of the viscous fluid bodily waste accepted by the structure. An alternative performance parameter in describing the penetration of a structure by VFBW is "receptivity". As used herein, the term "receptivity" refers to the penetration of a structure by a fluid per unit area per unit of power when subjected to the conditions set forth in the Receptivity Under Pressure test, described in the Test Methods section. Receptivity Under Pressure, or "receptivity" is measured as the amount of material that penetrates the surface of the structure per unit area per unit of power. "Power" is a term referring to amount of work done as a function of time (i.e., the rate at which work is done).

In preferred embodiments, the absorbent article of the present invention should include a waste management element 120 having an Acceptance Under Pressure of greater than about 0.5 g of viscous fluid bodily waste per square inch of the waste management element 120 per mJ (millijoule) energy input. More preferably, the waste management element 120 should have an Acceptance Under Pressure of greater than about 0.6 $g/in^2/mJ$ of viscous fluid bodily waste. Even more preferably, the waste management element 120 should have an Acceptance Under Pressure of greater than about 0.8 $g/in^2/mJ$, and most preferably greater than about 1.0 $g/in^2/mJ$ of viscous fluid bodily waste. Generally, Acceptance Under Pressure values between at least about 0.6 $g/in^2/mJ$ and about 10.0 $g/in^2/mJ$, and between about 0.8 $g/in^2/mJ$ and about 10.0 $g/in^2/mJ$ have been found to be acceptable. Alternatively, the waste acceptance element 120 should have a Receptivity Under Pressure of at least about 1.5 grams of viscous fluid bodily waste per square inch of the waste management element 120 per milliwatt (mW) of power, more preferably greater than about 3.0 $g/in^2/mW$, even more preferably greater than about 5.0 $g/in^2/mW$, most preferably greater than about 10.0 $g/in^2/mW$. Generally, the Receptivity Under Pressure is between about 1.5 and 50.0 $g/in^2/mW$ and may be between about 5.0 and about 50.0 $g/in^2/mW$. (These preferred Acceptance and Receptivity Under Pressure parameters relate to integrated articles which are preferably evaluated as they are intended for use. That is, if the article intended for use comprises more than one component or layer, all of the components or layers of the article should be configured as they would be during normal use when the measurement of their performance is made. A more detailed description of the method for determining Acceptance Under Pressure performance is included in the Test Methods section, below.)

If the Acceptance Under Pressure performance is too low, more work must be done (i.e., more energy input to the system) to cause the viscous fluid bodily waste to penetrate the waste management element 120. This is important because the energy available to push the viscous fluid bodily waste into the waste management element 120 is limited and varies from wearer to wearer and wearing cycle to wearing cycle. If the Receptivity Under Pressure is too low, more power is required (i.e., a given amount of energy input is required over a longer period of time) to cause viscous fluid bodily waste to penetrate the waste management element 120. This is important because many sources of energy in actual usage conditions are of short duration (e.g., wearer movements). Further, the properties of the viscous fluid bodily waste vary considerably between different wearers. Therefore, the absolute amount of viscous fluid bodily waste that will penetrate a structure having a high viscous fluid bodily waste penetration per unit work or per unit power will be greater than the amount that will penetrate a structure having a lower acceptance. High acceptance or receptivity values are also important to the overall performance of an absorbent article because only the portion of a viscous fluid bodily waste discharge that is accepted can be stored and immobilized.

Once viscous fluid bodily waste has penetrated the waste management element 120, it is desirable to store or hold the waste away from the wearer during the remainder of the wearing cycle and away from the caregiver during the changing process. As used herein, the term "store" refers to the physical separation of material deposited in a diaper from the body-facing surface of the article such that the material deposited in the diaper is not immediately in contact with or accessible to the wearer's skin. Storage Under Pressure, or "storage," is measured as the amount of material held in the structure on a unit area basis, as described in the Test Method Section below. If the Storage Under Pressure capacity is too low, the absolute quantity of viscous fluid bodily waste that can be stored away from skin access per unit area of the structure will be reduced. Adequate storage capacity is essential to reduce the probability of leakage and the area of skin contaminated by viscous fluid bodily waste because viscous fluid bodily waste that has been stored is less likely to be available to the body-facing surface of the structure for leakage and migration within the article.

In preferred embodiments of the present invention the absorbent article should include a waste management element 120 having a Storage Under Pressure value greater than about 0.70 grams per square inch ($g/in^2$) of the waste management element 120 of viscous fluid bodily waste. More preferably, the waste management element 120 should have a Storage Under Pressure value greater than about 0.80 $g/in^2$ of viscous fluid bodily waste. Even more preferably, the waste management element 120 should have a Storage Under Pressure value greater than about 1.0 $g/in^2$ of viscous fluid bodily waste, and most preferably greater than about 1.2 $g/in^2$ of viscous fluid bodily waste. Generally, Storage Under Pressure values between at least about 0.8 $g/in^2$ and about 10.0 $g/in^2$, and between about 1.0 $g/in^2$ and about 10.0 $g/in^2$ have been found to be acceptable. (These preferred Storage Under Pressure parameters relate to integrated articles which are preferably evaluated as they are intended for use. Accordingly, all of the components or layers of the article should be configured as they would be during normal use when the measurement of their performance is made. A more detailed description of the method for determining Storage Under Pressure performance is included in the Test Methods section, below.)

Figure 11:
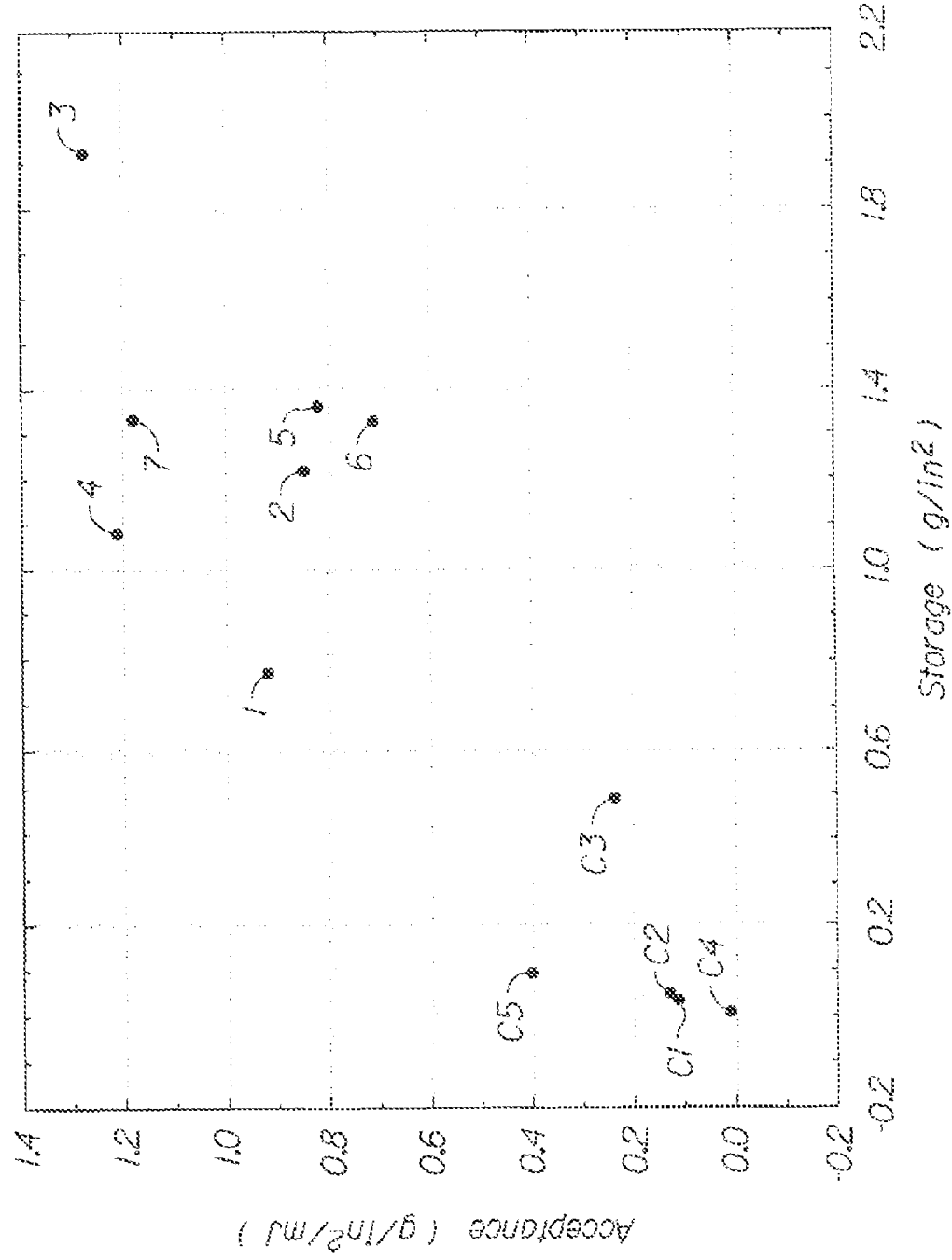
FIG. 11 is a 2-dimensional graphical representation of the relationship between Acceptance Under Pressure and Storage Under Pressure values of exemplary structures.

The Storage Under Pressure parameter is different from the Acceptance or Receptivity Under Pressure parameters in that it is an absolute measure of the quantity of viscous fluid bodily waste that can be imbibed within the structure on a unit area basis under a given applied pressure. Acceptance or receptivity, on the other hand, is a measure of the amount of material imbibed normalized by the amount of energy that was expended or power that was input, respectively, to force the material to penetrate the structure. Although each of the numbers is of value by itself, it is the combination of these parameters that gives a more accurate picture of the overall performance of a given structure. For example, the storage capacity of a structure may not be fully utilized if the energy required to "fill" the capacity is higher than the energy available in a given usage situation. Conversely, the acceptance of a structure may be high (i.e., energy required to penetrate is low), but the storage capacity may be very low, reducing the overall efficiency of the structure. Therefore, it is important to provide structures which have both an adequate viscous fluid bodily waste capacity and which require a minimum of energy input (work) or power to fill the available capacity. FIG. 11 is a graphical representation of the relationship between Acceptance and Storage Under Pressure values of several structures which are described in the Examples below.

Viscous fluid bodily waste that is accepted by, or penetrates, the absorbent article is preferably also retained in the diaper away from the wearer. One preferred way to retain bodily waste, especially viscous fluid bodily waste, is to immobilize the waste in a location away from the wearer. As used herein, the term "immobilize" refers to the ability of the material or structure to retain stored viscous fluid bodily waste under an applied pressure and/or the influence of gravitational forces Immobilization Under Compressed Inversion, or "immobilization," may be accomplished by increasing the waste's viscosity (e.g., by dewatering), by mechanical entrapment (i.e., a surface energy phenomenon driven by increased surface area of contact of the viscous fluid bodily wastes with the internal regions of the material or structure) or by any other means known in the art. "Immobilization Under Compressed Inversion," as described further in the Test Method Section below, is measured in terms of the percentage of the viscous fluid bodily waste or analog that remains in the structure after the structure is subjected to an inverted pressure cycle, as described below. "Retention Under Compressed Inversion", or "retention," is an absolute measure of how much viscous fluid bodily waste remains "stored" under stressful usage conditions.

Preferably, the waste management element 120 should have a Retention Under Compressed Inversion value of greater than about 7.5 g of the viscous fluid bodily waste which penetrates the structure. More preferably, the waste management element 120 should have a Retention Under Compressed Inversion value of greater than about 8.0 g of viscous fluid bodily waste, and most preferably greater than about 8.5 g of viscous fluid bodily waste after being subjected to the Retention Under Compressed Inversion test, as described below. Generally, Retention Under Compressed Inversion values between at least about 7.5 g and about 100.0 g, and between about 8.0 g and about 100.0 g have been found to be acceptable. Under the same conditions, the waste management element 120 should have an Immobilization Under Compressed Inversion value of at least 70% of the viscous fluid bodily waste accepted by the waste management element 120. More preferably, the waste management element 120 should have an Immobilization Under Compressed Inversion value of at least about 80% and most preferably at least about 85% of the viscous fluid bodily waste accepted by the element 120. Generally, Immobilization Under Compressed Inversion values between at least about 70% and about 100%, and between about 80% and about 100% have been found to be acceptable. (These preferred Immobilization and Retention Under Compressed Inversion parameters relate to integrated articles which are preferably evaluated as they are intended for use. Accordingly, all of the components or layers of the article should be configured as they would be during normal use when the measurement of their performance is made. A more detailed description of the method for determining Immobilization and Retention Under Compressed Inversion performance is included in the Test Methods section, below.)

Figure 9:
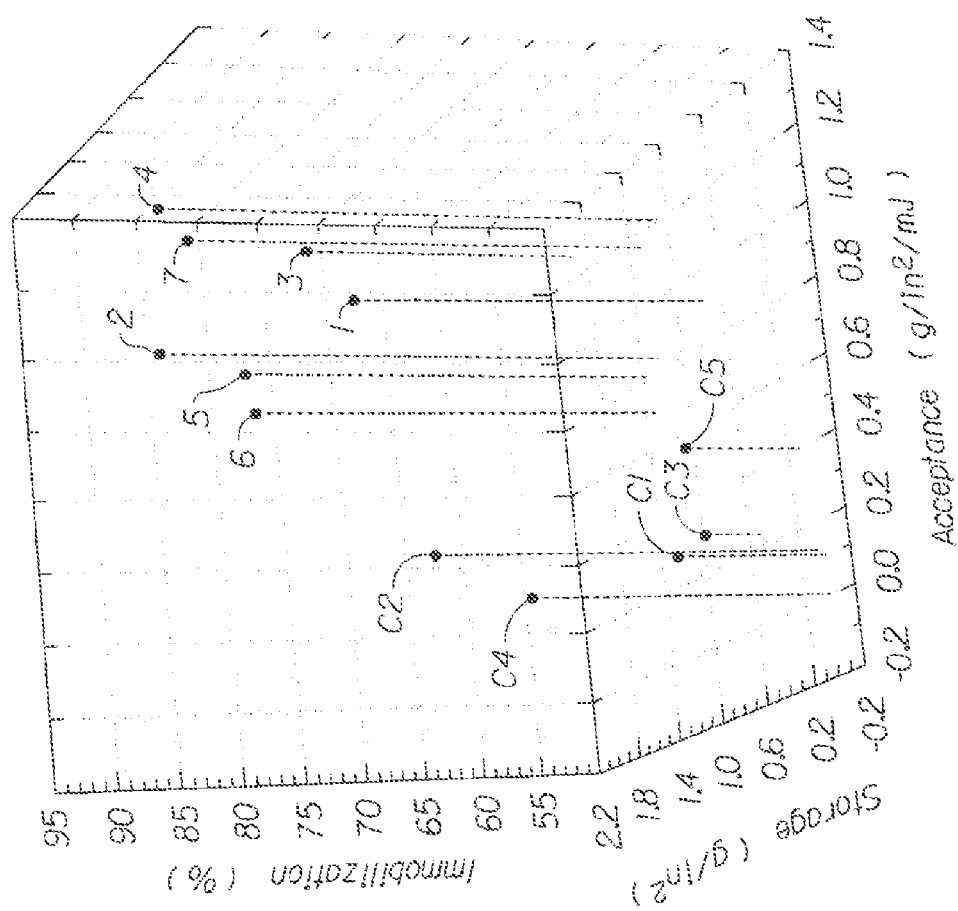
FIG. 9 is a 3-dimensional graphical representation of the relationship between Acceptance Under Pressure, Storage Under Pressure and Immobilization Under Compressed Inversion values of exemplary structures.
Figure 10:
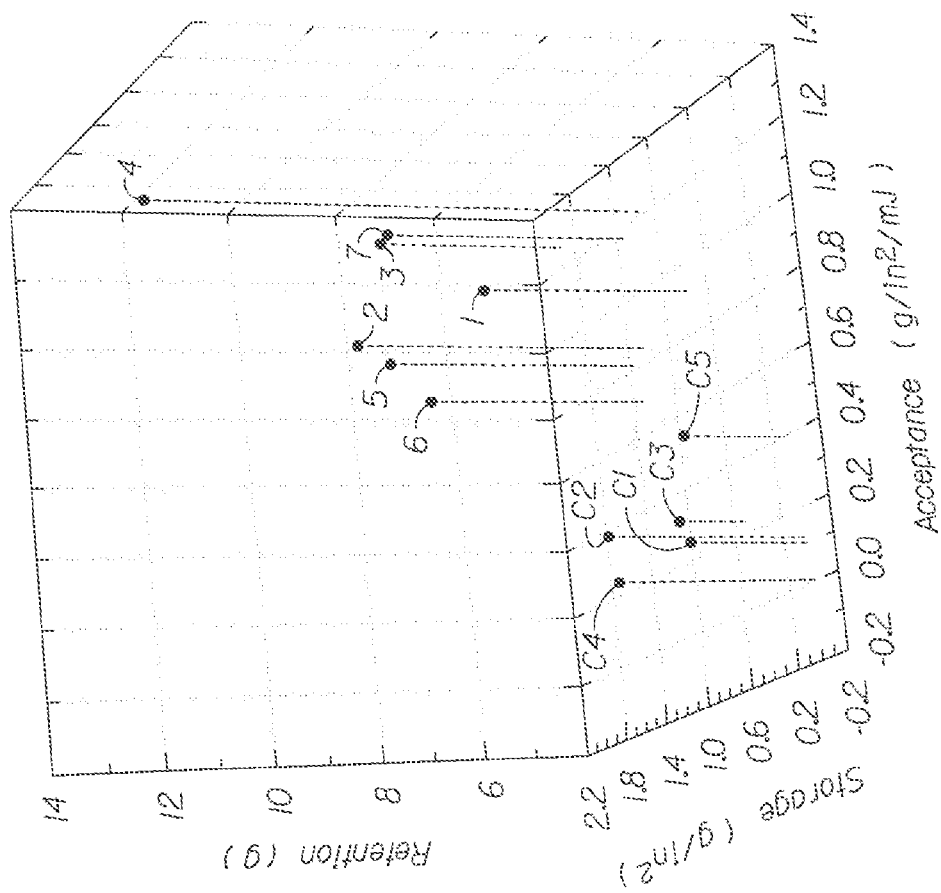
FIG. 10 is a 3-dimensional graphical representation of the relationship between Acceptance Under Pressure, Storage Under Pressure and retention values of exemplary structures.

Without the appropriate immobilization and retention performance, the effects of improved acceptance and storage performance may be diminished because the viscous fluid bodily waste may return to the body-facing surface of the structure, increasing the likelihood of leakage or contamination of the wearer's skin. Further, immobilization is most effective if the structure first accepts the waste and then stores it. Viscous fluid bodily waste that is immobilized prior to being stored away from the wearer's skin may remain on the topsheet in contact with the skin Immobilizing viscous fluid bodily waste which is in contact with the skin can increase the effort required by the caregiver during the changing/cleaning process and increases the likelihood of residual, micro-level contamination. "Micro-level contamination" refers to waste residue which remains on the skin, but is not easily visible to the human naked eye. Therefore, as shown in the graph of FIGS. 9 and 10, it may be helpful to consider at least three parameters (acceptance, storage, and immobilization or acceptance, storage and retention) for a given structure when determining its utility for effectively managing viscous fluid bodily wastes.

Although structures which accept, store and immobilize viscous fluid bodily wastes are preferred, in certain embodiments of the present invention, the waste management element 120 may comprise only an acceptance element, a storage element or an immobilization element, or may include a combination of two of the elements, but not the third. Also, in certain embodiments, one element may perform more than one function (e.g., a storage element may perform both the storage and immobilization functions). For example, the absorbent article of the present invention may include an acceptance and a storage element to manage viscous fluid bodily wastes without a separate immobilization element, per se. Accordingly, it is desirable to be able to identify suitable individual acceptance, storage and immobilization elements and to measure their effectiveness separate from an integral absorbent article structure. The following discussion identifies several, but not all, suitable acceptance, storage and immobilization elements which can be used independently of each other or in any combination and a preferred method of determining their relative effectiveness.

Acceptance Element

In a preferred embodiment of the present invention, the waste management element 120 includes an acceptance means or acceptance element 150. The acceptance element 150 is that portion of the diaper 20 which is intended to accept bodily exudates deposited in the diaper 20, and more particularly is intended to accept viscous fluid bodily waste. The acceptance element 150 preferably should have an Acceptance Under Pressure value of greater than 0.70 $g/in^2/mJ$ of viscous fluid bodily waste or an equivalent analog. More preferably, the acceptance element 150 should have an Acceptance Under Pressure value of greater than 0.8 $g/in^2/mJ$, and most preferably greater than 1.0 $g/in^2/mJ$ of viscous fluid bodily waste. Generally, Acceptance Under Pressure values between at least about 0.6 $g/in^2/mJ$ and about 10.0 $g/in^2/mJ$ and between about 0.8 $g/in^2/mJ$ and about 10.0 $g/in^2/mJ$ have been found to be acceptable. Alternatively, the acceptance element 150 should have a Receptivity Under Pressure of at least about 1.5 grams of viscous fluid bodily waste per square inch of the acceptance element 150 per milliwatt (mW) of power, more preferably greater than about 3.0 $g/in^2/mW$, even more preferably greater than about 5.0 $g/in^2/mW$, most preferably greater than about 10.0 $g/in^2/mW$. Generally, the Receptivity Under Pressure is between about 1.5 and 50.0 $g/in^2/mW$ and may be between about 5.0 and 50.0 $g/in^2/mW$. If the acceptance or receptivity performance is too low, more work must be done, or more power applied, respectively, (i.e., more energy input to the system) to cause the viscous fluid bodily waste to penetrate the acceptance element 150. As noted above, high Acceptance or Receptivity Under Pressure performance is important to the overall performance of an absorbent article because waste which is not accepted will stay in contact with the wearer's skin. Further, only the portion of a viscous fluid bodily waste that is accepted can be stored and immobilized away from the wearer's skin, as contemplated by the present invention.

The acceptance element 150 may be any material or structure capable of accepting bodily exudates, as described above. The acceptance element 150 may include a single material or a number of materials operatively associated with each other. Further, the acceptance element 150 may be integral with another element of the diaper 20 or may be one or more separate elements joined directly or indirectly with one or more elements of the diaper 20. Further, any or all of the acceptance element 150 may be removable from the absorbent article for separate disposal, if desirable.

The acceptance element 150 is preferably disposed at least partially in the crotch region 37 of the diaper 20 adjacent the body surface 47 of the core 28, although in some alternate embodiments, the acceptance element 150 may include at least a portion of a leg cuff, waistband, fecal waste containment pocket, or the like, or may be operatively associated with any such features. Preferably, at least the portion of the acceptance element 150 located in the region of diaper 20 which is near the anus of the wearer during use is unobstructed by overlying layers of structures, such as the topsheet 24. Thus, it may be desirable to cut out a portion of the topsheet 24 in the region of the article intended to be located near the wearer's anus and to provide an acceptance element 150 as the body-side liner in that region. Alternatively, any or all of the topsheet 24 may be made or treated to act as the acceptance element 150. In one embodiment, as shown in FIG. 1, the acceptance element 150 includes at least a portion of the topsheet 24. In other embodiments, the acceptance element 150 may include at least a portion of other elements of the diaper such as the absorbent core 28 or the storage element (described below).

In some embodiments, it may be desirable to provide the diaper 20 with different acceptance or receptivity performance in different portions of the diaper. This may be accomplished by providing different acceptance elements in the different regions of the diaper 20 or by providing a single acceptance element 150 which has been manufactured or treated to have regions of differing acceptance characteristics. Further, the acceptance element 150 may be elevated above the plane of the body-facing surface of the article so as to be in better control of exuded viscous fluid bodily wastes. In some embodiments, it may even be desirable to have the acceptance element 150 in contact with skin of wearer in proximity of the viscous fluid bodily waste source (e.g., the perianal region).

Suitable materials and structures for use as the acceptance element 150 may include apertured nonwoven webs, apertured films, apertured formed films, scrims, woven webs, scrim, netting, macroporous thin foams, and the like. One particularly preferred material is a woven netting available as a Toy Tub Bag from Dollar Tree Dist., of Norfolk, Va. Further, the acceptance element 150, or any portion thereof, may be coated with a lotion or other known substances to add, enhance or change the performance or other characteristics of the element. For example, the acceptance element 150 may be hydrophobic or hydrophilic or treated to be either.

Figure 4:
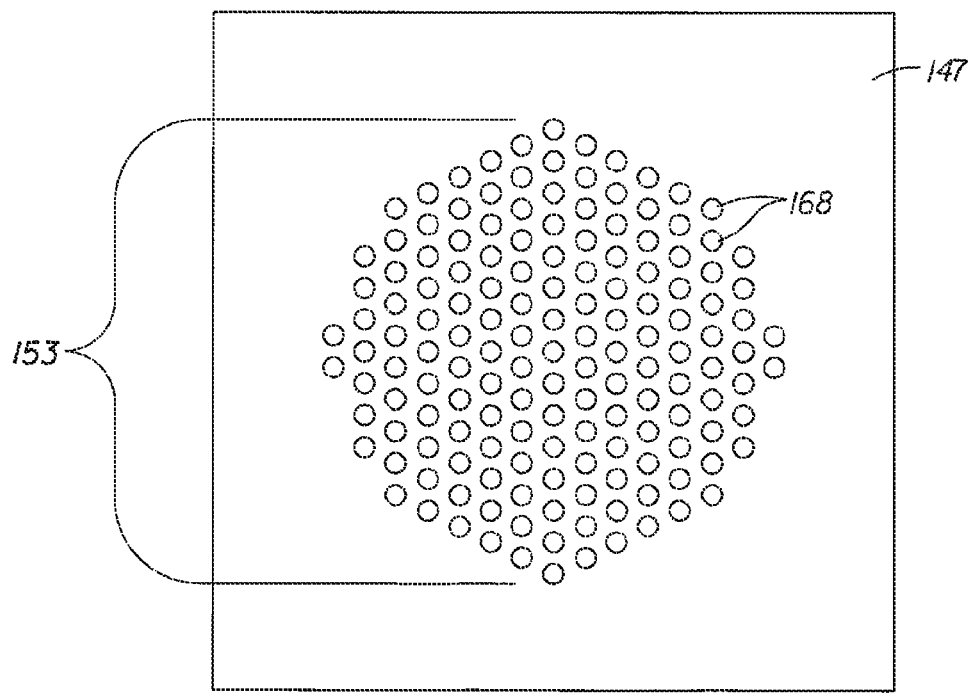
FIG. 4 is a plan view of a piece of the apparatus shown in FIG. 3.

Table I shows the Acceptance and Receptivity Under Pressure performance of several materials. Acceptance and Receptivity Under Pressure data for the individual acceptance elements shown in Table I is generated via the same method as Acceptance and Receptivity Under Pressure data for the integral samples tested below, except that the samples tested for Table I include only the acceptance element 150. Further, the acceptance element 150 is tested in conjunction with a standard storage element 147 rather than the underlying structure of the absorbent article from which the acceptance element 150 was taken. (The standard storage element 147 includes a 4 inch square 1.6 millimeter thick aluminum plate having a pattern of 153 regularly spaced 4.3 millimeter diameter holes 168, as shown in FIG. 4. The holes are arranged such that there are approximately 26 holes per square inch.)

TABLE I

Acceptance Under Pressure Using a Standard Storage Element

| Acceptance Element | Acceptance Under Pressure (g/in²/mJ) | Receptivity Under Pressure (g/in²/mW) |
| --- | --- | --- |
| Hydroentangled, apertured nonwoven web GH437 from Chicopee Inc., North Charleston, SC | 0.45 | 1.65 |
| Apertured vacuum-formed film X-3265 from Tredegar Corp. of Terre Haute, IN | 0.16 | 0.27 |
| Woven netting (Toy Tub Bag) from Dollar Tree Dist., of Norfolk, VA | 3.54 | 4.49 |

One parameter in obtaining suitable acceptance and receptivity performance has been found to be related to the total effective open area of the acceptance element 150. Preferably, the effective open area of the acceptance element 150 is at least about 30%, more preferably at least about 50%, and most preferably at least about 70%. Typically, the effective open area of the acceptance element 150 should be in the range of about 30 to 70%. Such effective open area values and ranges are necessary to ensure that the waste can easily enter or pass through the acceptance element 150 to the absorbent core, storage element 152 or other underlying structure. This is important because the improved storage and/or immobilization characteristics of the present invention are less likely to be achieved if a sufficient portion of the waste does not penetrate the acceptance element 150.

Figure 19:
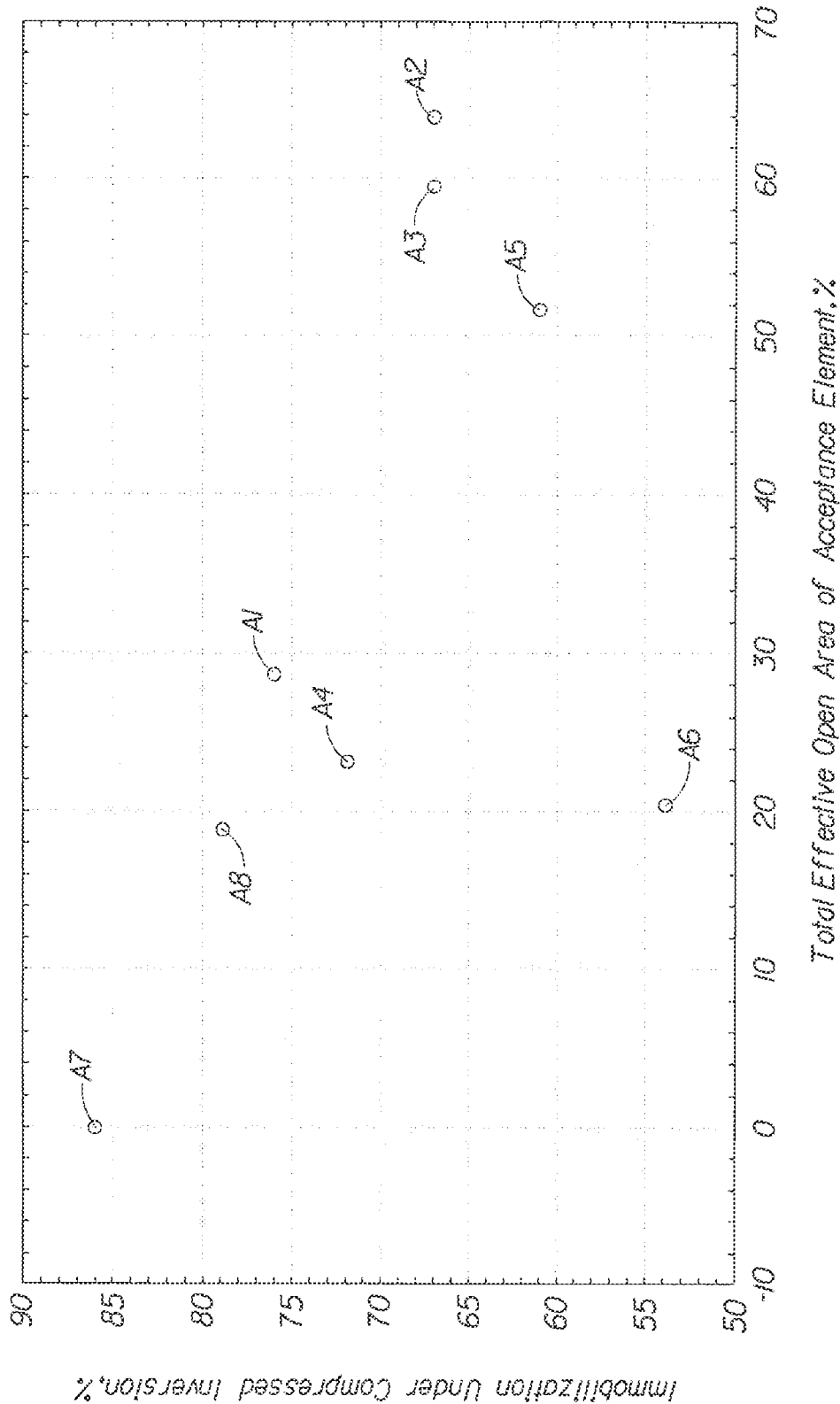
FIG. 19 is a 2-dimensional graphical representation of the relationship between Immobilization Under Compressed Inversion values of exemplary structures and the Effective Open Area of an associated acceptance element.
Figure 20:
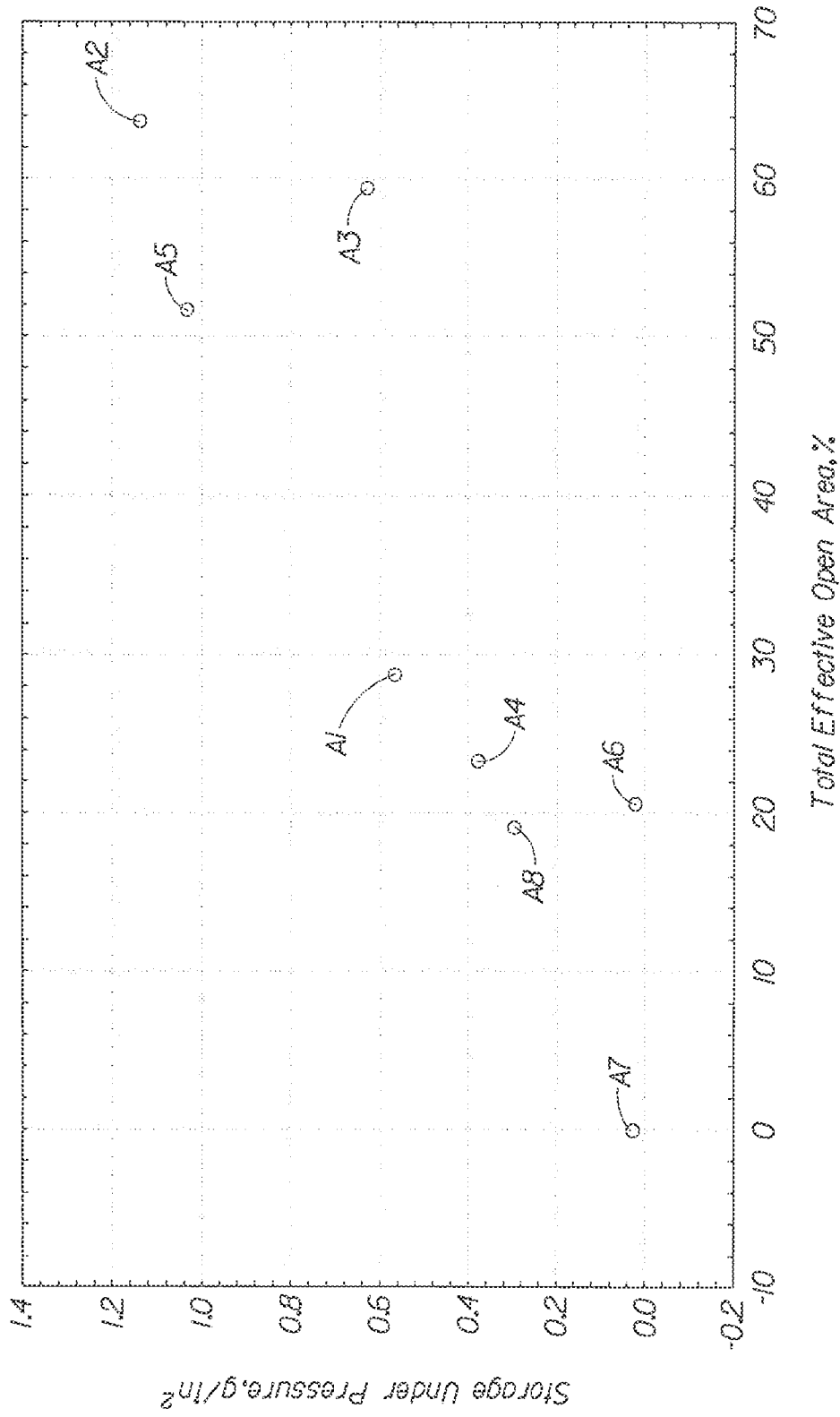
FIG. 20 is a 2-dimensional graphical representation of the relationship between Storage Under Pressure values of exemplary structures and the Effective Open Area of an associated acceptance element.
Figure 21:
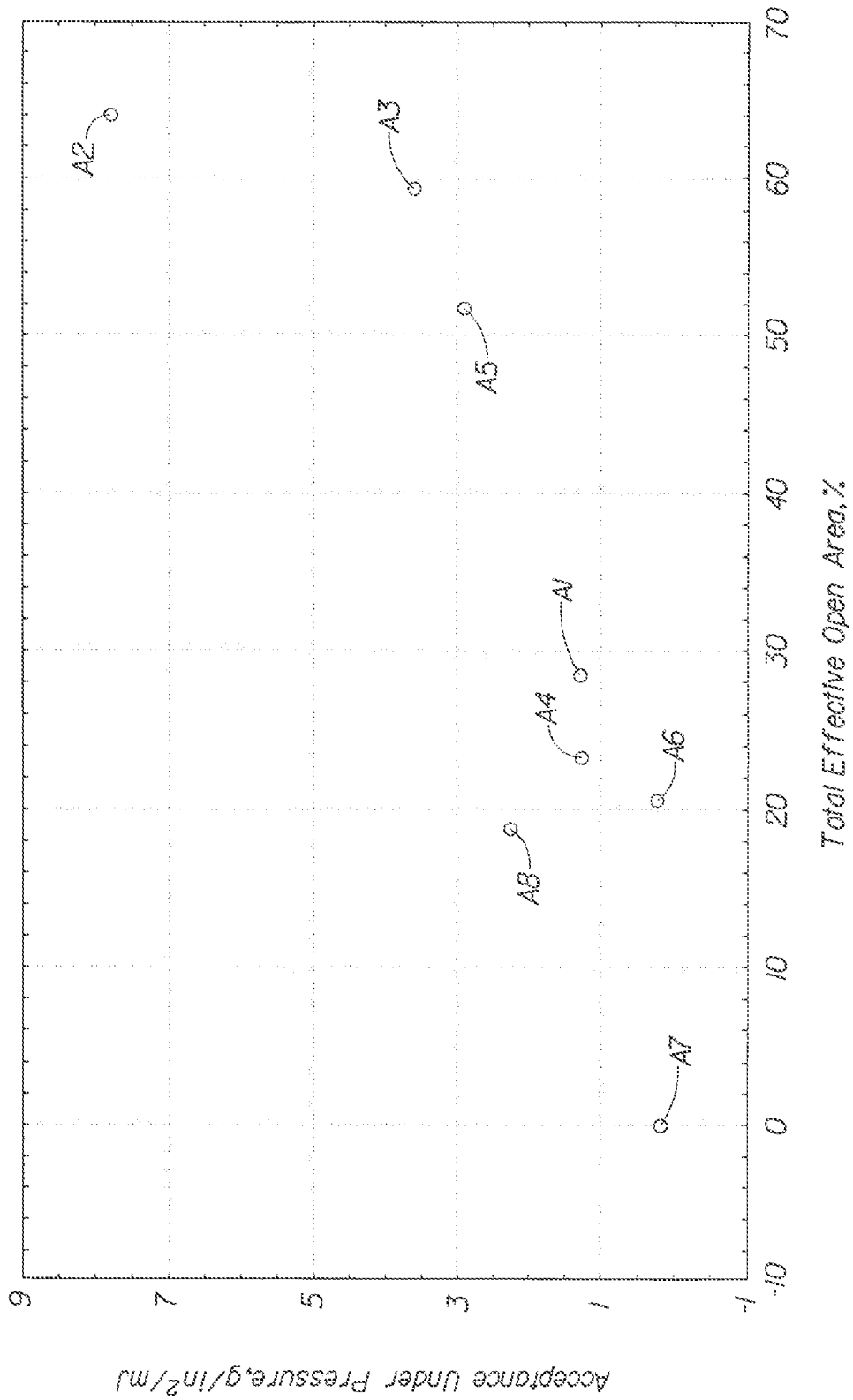
FIG. 21 is a 2-dimensional graphical representation of the relationship between Acceptance Under Pressure values of exemplary structures and the Effective Open Area of an associated acceptance element.
Figure 22:
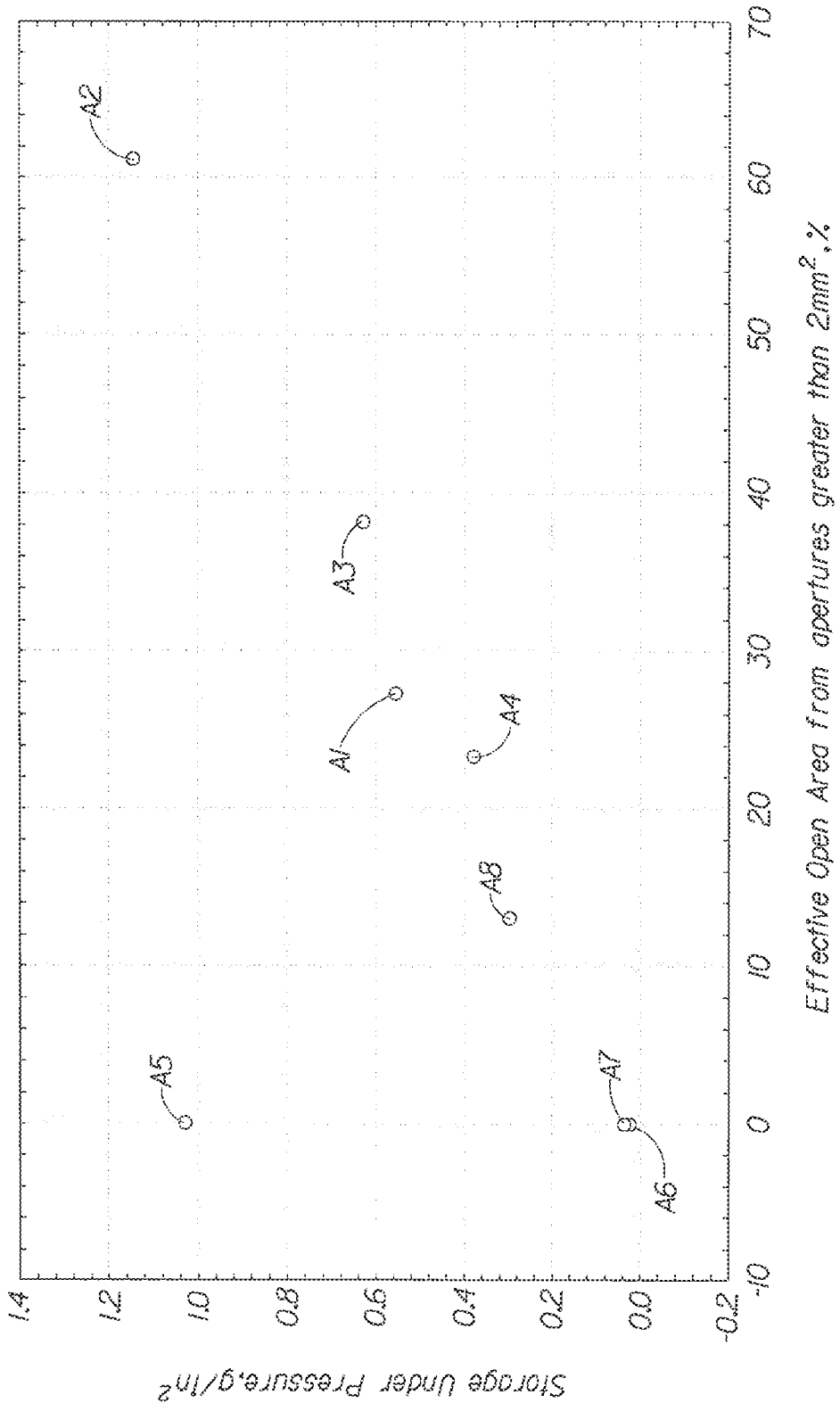
FIG. 22 is a 2-dimensional graphical representation of the relationship between Storage Under Pressure values of exemplary structures and the Effective Open Area of an associated acceptance element.

To achieve suitable total effective open area measurements, the acceptance element 150 may include apertures. If the acceptance element 150 includes apertures, the apertures preferably have an effective aperture size of at least 0.2 square millimeters, more preferably at least 0.5 square millimeters, even more preferably at least 1.0 square millimeters, and most preferably at least 2.0 square millimeters. Generally preferred effective aperture sizes are between about 0.2 square millimeters and about 50 square millimeters, and more preferably between about 1.0 square millimeters and about 25 square millimeters. Table II shows the total effective open area and the effective open area contributed by apertures greater than 2.0 square millimeters for a number of exemplary web-like materials. The Acceptance, Receptivity, and Storage Under Pressure values for each of these materials in conjunction with the standard storage element is also shown. These data are also presented graphically in FIGS. 19-22. It is readily apparent from these data that the above-mentioned ranges for effective open area of the acceptance element are critical for superior waste management element performance in terms of immobilization (FIG. 19), storage (FIGS. 20 and 22), and acceptance (FIG. 21).

TABLE II

| Example | Acceptance Element Description | Total Effective Open Area, % | Effective Open Area from apertures >2.0 mm², % | Acceptance Under Pressure g/in2/mJ | Storage Under Pressure G/in2 | Receptivity Under Pressure, g/in2/mW |
| --- | --- | --- | --- | --- | --- | --- |
| A1 | Apertured Vacuum Formed Film X5790 (⅛" honeycomb pattern) from Tredegar, Corp of Terre Haute, IN | 28.5 | 27.0 | 1.24 | 0.56 | 8.99 |
| A2 | Woven netting Laundry Bag From LBU Inc., Carlstadt, NJ | 63.90 | 61.0 | 7.70 | 1.13 | 15.27 |
| A3 | Woven Netting (Tub Toy Bag) from Dollar Tree Norfolk, VA | 59.5 | 38.0 | 3.7 | 0.63 | 8.54 |
| A4 | Made from 50 g/m² Corovin LLDPE with secondary bond sites and ring rolled to produce a selectively apertured nonwoven (SAN) as described in US Pat. No. 5,628,097 | 23.3 | 23.0 | 1.25 | 0.39 | 6.55 |
| A5 | Standard Acceptance element 150 | 51.70 | 0.0 | 2.95 | 1.03 | 6.01 |
| A6 | A 30 g/m² hydrophobic apertured polypropylene nonwoven produced by Pantex from Pistoia, Italy and identified as PN-S-30 P3 HO | 20.40 | 0.0 | 0.15 | 0.01 | 0.24 |
| A7 | A 23.3 g/m² Carded Polypropylene nonwoven available as P-8 and produced by Fibertech of Franksville, WI. | 0.0 | 0.0 | 0.10 | 0.02 | 0.20 |

TABLE II-continued

| Example | Acceptance Element Description | Total Effective Open Area, % | Effective Open Area from apertures >2.0 mm², % | Acceptance Under Pressure g/in2/mJ | Storage Under Pressure G/in2 | Receptivity Under Pressure, g/in2/mW |
|---------|-------------------------------|------------------------------|-----------------------------------------------|-----------------------------------|------------------------------|--------------------------------------|
| A8 | A 32 g/m² duo-layer phased polypropylene apertured nonwoven identified as #97/037 and produced by Amoco Fabrics, Germany | 19.0 | 13.0 | 2.08 | 0.29 | 4.14 |

The effective aperture size and percentage open area can be determined by the procedure described at Col. 10, line 44-Col. 12, line 43 of U.S. Pat. No. 5,342,338 entitled "Disposable Absorbent Article For Low-Viscosity Fecal Material" issued to Roe on Aug. 30, 1994, which is hereby incorporated by reference herein.

Storage Element

The waste management element 120 of the present invention preferably also includes a storage means or storage element 152 capable of storing viscous bodily wastes accepted by the acceptance element 150 or other overlying layer(s), if any. In preferred embodiments, the storage element 152 should have a Storage Under Pressure value of about 0.70 g/in² of viscous fluid bodily waste. More preferably, the storage element 152 should be able to store greater than about 0.80 g/in² of viscous fluid bodily waste. Even more preferably, the storage element 152 should be able to store greater than about 1.0 g/in² of viscous fluid bodily waste, and most preferably greater than about 1.2 g/in² of viscous fluid bodily waste. Generally, Storage Under Pressure values between at least about 0.8 g/in² and about 10.0 g/in² and between about 1.0 g/in² and about 10.0 g/in² have been found to be acceptable.

Figure 5:
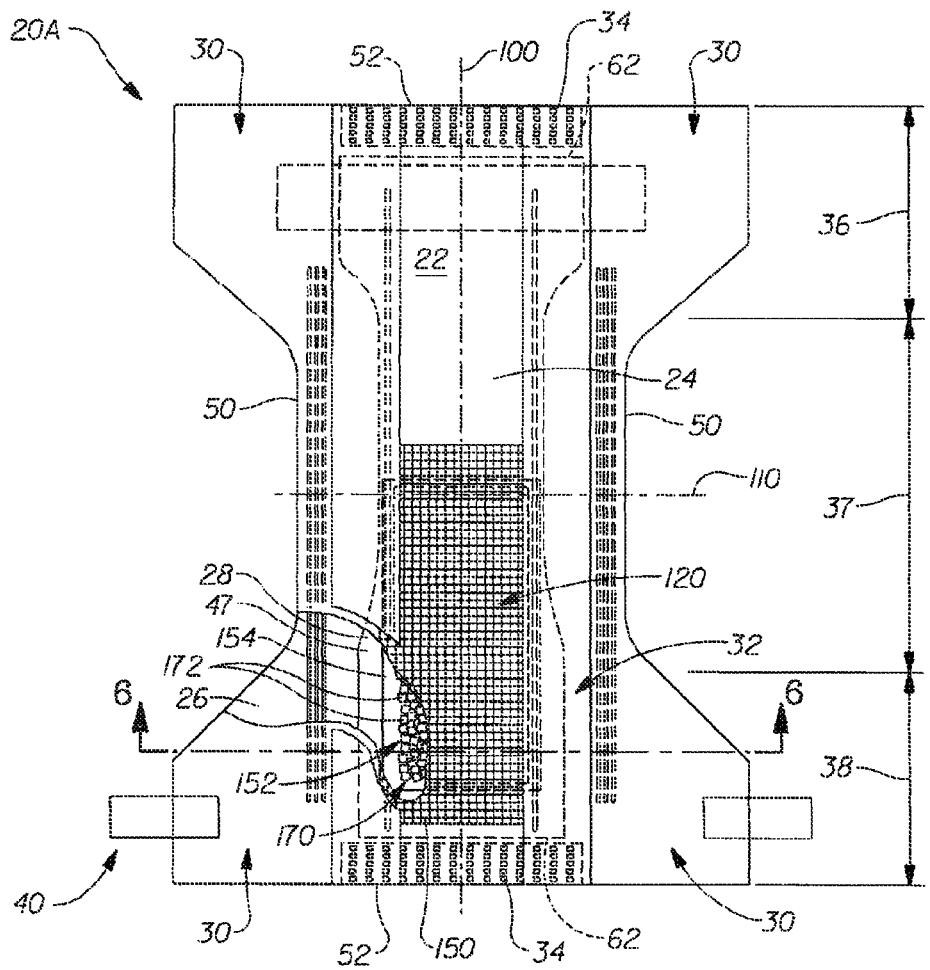
FIG. 5 is a plan view of one embodiment of the present invention having portions cut away to reveal the underlying structure, the body facing surface of the diaper facing the viewer.
Figure 6:
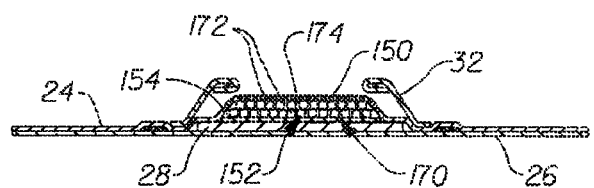
FIG. 6 is a cross sectional view of the diaper of FIG. 5 taken through 6-6.
Figure 6A:
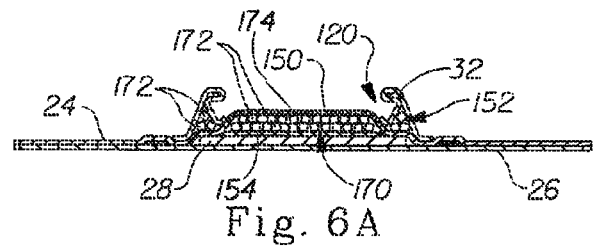
FIG. 6A is a cross sectional view of an alternative embodiment of the present invention.

The storage element 152 may be located anywhere in the diaper 20. However, it is preferred that the storage element 152 be operatively associated with the acceptance element 150 and/or topsheet 24, if any, such that viscous fluid bodily waste accepted by the acceptance element 150 may enter the storage element 152. (Embodiments are contemplated wherein the diaper 20 has no topsheet 24 or acceptance element 150. In such cases, the bodily waste may enter the storage element 152 directly, without passing through any overlying structure.) In any case, it is preferred that the storage element 152 be located in the region of the diaper 20 which is located near the wearer's anus when the diaper 20 is worn. Accordingly, it is preferred that at least a portion of the storage element 152 be disposed in the crotch region 37 of the absorbent article. However, in some alternate embodiments, the storage element 152 may include at least a portion of either waist region (as shown in FIGS. 5 and 6, for another embodiment 20A of the present invention, in the second waist region 38), a leg cuff (as shown in FIG. 6A for the embodiment 20A), the waistband, a fecal waste containment pocket, or the like, or may be operatively associated with any such features. Further, the storage element 152 may be elevated above the plane of body-facing surface of the article so as to be in better control of exuded viscous fluid bodily wastes. In some embodiments, it may even be desirable to have the storage element 152 in contact with skin of wearer in proximity of the viscous fluid bodily waste source (e.g., the perianal region).

The Storage Under Pressure performance of the storage element 152 may be uniform or may vary throughout the diaper 20. Such variations may be accomplished by employing multiple storage elements 152 in the diaper 20 or by providing a single storage element 152 with regions of different Storage Under Pressure capacities. Further, any or all of the storage element 152 may be removable from the absorbent article for separate disposal, if desirable.

The storage element 152 may be any material or structure capable of storing bodily exudates, as described above. Thus, the storage element 152 may include a single material or a number of materials operatively associated with each other. Further, the storage element 152 may be integral with another element of the diaper 20 or may be one or more separate elements joined directly or indirectly with one or more elements of the diaper 20. In one embodiment, as shown in FIG. 5, the storage element 152 includes a structure that is separate from the core 28. However, embodiments are contemplated wherein the storage element 152 includes at least a portion of the core 28.

Suitable materials for use as the storage element 152 may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a fibrous looped material, vertically oriented strands of looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and more specifically, having pores greater than about 1.0 mm in diameter.) One embodiment includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. The storage element 152, or any portion thereof, may include or be coated with a lotion or other known substances to add, enhance or change the performance or other characteristics of the element.

An alternate embodiment of a storage element 152 includes a macro-particulate structure 170 comprising a multiplicity of discrete particles 172, nonlimiting examples of which are shown as FIGS. 5 and 6. The macro particles 172 preferably have a nominal size, preferably between about 1.0 mm and about 25.4 mm, and more preferably between about 2 mm and about 16 mm. However, particles as small as 0.5 mm and smaller, and particles larger than about 25.4 mm are contemplated. Particles having a nominal size of about 1.0 mm or greater are those which are generally retained on the surface of a U.S. Standard No. 18 mesh sieve screen. Particles having a nominal size of less than about 25.4 mm are those which generally pass through a U.S. Standard 25.4 mm sieve screen. Particles having a nominal size of 16 mm or greater are those which are generally retained on the surface of a U.S. Standard No. 16 mm sieve screen. The nominal particle size is measured prior to incorporating the particles into a storage element 152 for testing or use. Particles having a nominal size of 8 mm or greater are those which are generally retained on the surface of a U.S. Standard 8 mm sieve screen.

The macro-particulate structure 170 may include any number of particles 172. Further, the particles 172 may be unjoined and free to move within the structure 170 or may be joined to each other by any known means. Alternatively, the structure 170 may include an external support, such as a meltblown hot-melt glue, a web, a netting, a scrim, a thread or other adhesive or nonadhesive entangling supports. Any of the particles 172 may also be joined with any other portion of the diaper structure, such as the topsheet or the core. The particles 172 may also be constrained in patterned, three-dimensional regions such as pleats, "pillows", and pockets.

The individual particles 172 may be made from any material suitable for use in absorbent articles, including the materials described above with regard to the absorbent core 28 or the storage element 152. The materials used in the particles 172 may be absorbent, nonabsorbent, microporous, macroporous, resilient, nonresilient, etc. or may have any other desirable characteristic. Examples of macroporous absorbent materials suitable for use in the particles 172 include highloft nonwovens, open cell foams, bundles of fibers, sponges and the like. Other absorbent materials include cellulosic batts, capillary channel fibers, osmotic storage materials such as superabsorbent polymers, etc. Non-absorbent particles 172 may comprise plastic, metal, ceramic, glass, closed cell foams, column packing materials, synthetic fibers, gels, encapsulated gas, liquids and the like. Further, any or all of the particles 172 may include odor absorbents, lotions, skin care formulations, antimicrobials, pH buffers, enzyme inhibitors, and the like.

The storage element 152 may comprise a single type of particle 172 (size, shape, material, etc.) or may include a mixture of different particles 172. The mixture may be homogeneous; heterogeneous, as when particles 172 having different properties are disposed in certain areas of the storage element 152; layered; or any other desirable configuration. In some embodiments, more than one type of mixture may be employed (e.g., macroporous and nonabsorbent particles 172 may be homogeneously mixed in one layer while another layer includes only absorbent particles.) Different layers of particles may be directly adjacent each other or may be separated by one or more materials, such as netting, scrim, non-woven or woven webs, film, foam, adhesive, and the like.

The macro-particulate structure 170 preferably includes a continuous interstitial void space 174 that is defined by the space between the particles 172. By varying the size and/or shape of the particles 172, the interstitial void space 174 can be controlled. The particles may be of any known shape, including spheres, oblate spheroids, rectangular and polygonal solids, and the like. Table III shows the void fractions of particles having particular alternative shapes and nominal sizes. Other suitable shapes and void fractions are described in Perry's Chemical Engineering Handbook, 6th ed., McGraw-Hill, 1984, at p. 18-20.

TABLE III

| Packing Type | Nominal Size (mm) | Void Fraction |
|---|---|---|
| Berl saddles | 6 | 0.60 |
|  | 13 | 0.62 |
| Intalox saddles | 6 | 0.75 |
|  | 13 | 0.78 |
| Pall rings | 16 | 0.87-0.92 |
| Raschig rings | 6 | 0.62 |
|  | 13 | 0.64 |
|  | 19 | 0.72 |

Regardless of the makeup of the storage element 152, it should resist compression so as to maintain some significant level of capacity (e.g., "storage") when a compressive force is applied to the storage element 152. This property is referred to as the "compressive resistance" of the storage element. Preferably, the storage element 152 is able to maintain at least about 50% of its original thickness when a compressive force of 0.2 psi is applied to the structure (i.e., have a compressive resistance of at least about 50%). More preferably, the storage element 152 should be able to maintain at least about 70%, even more preferably at least about 80%, and most preferably at least about 90% of its original thickness when a compressive force of 0.2 psi is applied. Generally, in preferred embodiments, the storage element 152 is able to maintain between about 50% and 99% of its original thickness when a compressive force of 0.2 psi is applied to the structure. More preferably, the storage element 152 should be able to maintain between about 70% and 95% of its original thickness when a compressive force of 0.2 psi is applied. The storage element 152 should also be capable of restoring itself to substantially its original thickness when the force is removed. This property is referred to as the "resiliency" of the storage element. Preferably, the storage element 152 should recover at least about 80% of its original thickness (i.e., have a resiliency of at least about 80%), and more preferably at least about 90% of its original thickness after the compression force of 0.2 psi is removed.

In addition to its storage function, the storage element 152 may transport viscous fluid bodily waste within the absorbent article 20 in directions generally parallel to the plane of the backsheet 26. The transport may be active, such that capillary or other forces result in the movement of the viscous fluid bodily waste or components thereof (e.g., free water). In other embodiments, the transport may be passive whereby viscous fluid bodily waste or components thereof move through the structure under the influence of externally applied forces, such as gravity, wearer pressure or wearer motion. In the case of passive transport, the storage element 152 should have relatively large, interconnected channels, or the like, such that the viscous fluid bodily waste may readily move through the structure with minimum energy input.

Table IV includes Storage Under Pressure performance data relating to several individual storage element structures. Storage Under Pressure performance of individual storage elements 152 may be measured in the same manner as the Storage Under Pressure test described below with regard to integral structures, except that the individual storage elements 152 are tested separate from any other structure and under a standard acceptance element 150. The standard acceptance element 150 is a stainless-steel wire cloth Type 304 (Standard Grade) 16×16 mesh, available as #9226T45 from McMaster Carr Supply Company of Chicago, Ill.

TABLE IV

Storage Under Pressure Using a Standard Acceptance Element

| Storage Element | Storage Under Pressure (g/in$^2$) |
|---|---|
| Acquisition Layer from Pampers Premium Size 5 Diaper from P&G, Cincinnati, OH | 0.45 |
| Loop landing element of Comparative Example 5 without apertured vacuum-formed film topsheet | 0.52 |
| Large-cell formed film of Comparative Example 3 without hydroentangled apertured nonwoven web topsheet | 0.70 |
| Scrubber particles of Example 3 without woven netting topsheet | 1.14 |
| Mixture of scrubber particles and foam strips of Example 5 without woven netting topsheet | 1.80 |
| Layered assembly of scrubber particles and foam strips of Example 6 without woven netting topsheet | 1.89 |

Improved immobilization performance at lower compressive resistance may be achieved by including capillary channel fibers in the storage element 152. (See Example 16). For example, a storage element 152 may comprise fibrous loops of capillary channel fibers (oriented, for example, primarily in the z-direction) formed by needle-punching the fibers into a substrate. Storage volume is provided by the loop geometry itself. However, the capillary channel fibers, having capillary magnitude grooves on their exterior, are able to more aggressively retain the feces and/or analog under applied pressure. Acceptable capillary channel fibers are available as six denier/filament fibers identified as Code DPL-77A from Fiber Innovation Technology, Johnson City, Tenn. and are needle-punched into a substrate described as DFPN162 and produced by Fiberweb, Terre Haute, Ind. to create a looped, carpet-like structure. However, the storage element may also include other types of fibers with feces retention means other than capillary channels as well as non fibrous members providing feces retention capacity.

Improved immobilization performance at lower compressive resistance may also be achieved by creating layered structures comprising a relatively compressible top layer (i.e., closer to the wearer) having a macroporous open structure over a bottom layer (i.e., further from the wearer) comprising a relatively incompressible storage layer capable of retaining feces and/or analog (e.g., via a multiplicity of fibers, such as loops, to provide a large contact area). In one suitable embodiment, a macroporous polyurethane/polyester reticulated foam may be used. Preferably the foam should be of uncompressed thickness of between about 3 mm and 15 mm, and more preferably between about 4 mm and about 10 mm. The foam preferably has a nominal pore distribution of about 10 pores per inch (ppi). For example, a foam of about 6.3 mm thickness and nominal pore distribution of about 10 pores per inch (ppi) available as SIF/10 from Foamex of Eddystone, Pa., may be placed over a loop structure comprising a needle punched polypropylene loop carpet/floor mat with an uncompressed thickness of about 7 mm produced by Royal Rubber & Manufacturing Co. of South Gate, Calif. However, any other suitable number or combination of layers may be used including any of the acceptance and storage elements described herein or others known in the art or developed hereafter which provide the desired performance characteristics. For example, a macroporous compressible member, such as a reticulated foam, may be disposed between at least a portion of the acceptance element and at least a portion of the fibrous looped material.

Immobilization Element

In addition to or in place of either the acceptance element 150 or the storage element 152, the waste management element 120 of the present invention preferably includes an immobilization means or immobilization element 154. The immobilization element 154 should be capable of immobilizing and retaining viscous fluid bodily waste that is accepted and stored by the absorbent article. Preferably, the immobilization element 154 should have immobilization values corresponding to at least about 70% of the viscous fluid bodily waste accepted by the waste management element 120. More preferably, the immobilization element 154 should have immobilization values corresponding to at least about 80% and most preferably at least about 85% of the viscous fluid bodily waste accepted by the waste management element 120. Generally, Immobilization Under Compressed Inversion values between at least about 70% and about 100% and between about 80% and about 100% have been found to be acceptable. Further, the immobilization element 154 should be capable of retaining greater than about 7.5 g of viscous fluid bodily waste which penetrates the structure. More preferably, the immobilization element 154 should be able to retain greater than about 8.0 g of viscous fluid bodily waste, and most preferably greater than about 8.5 g of the viscous fluid bodily waste which penetrates the structure. Generally, Retention Under Compressed Inversion values between at least about 7.5 g and about 100.0 g and between about 8.0 g and about 100.0 g have been found to be acceptable.

The immobilization element 154 may be any material or structure capable of reducing the proclivity of viscous fluid bodily waste that has penetrated the immobilization element 154 from leaving the structure. Thus, the immobilization element 154 may include a single material or a number of materials operatively associated with each other. Further, the immobilization element 154 may be integral with another element of the diaper 20 or may be one or more separate elements joined directly or indirectly with one or more elements of the diaper 20. For example, the immobilization element 154 may be an unjoined layer of material disposed under the storage element 152 or may include all or a portion of the storage element 152 which is able to immobilize and retain viscous fluid bodily waste, as described above. In any case, it is preferred that the immobilization element 154 be operatively associated with the storage element 152 and the acceptance element 150. This is necessary to ensure that viscous fluid bodily waste accepted and/or stored by the article passes into or comes in contact with the immobilization element 154. Accordingly, it may be desirable to locate the immobilization element 154 below the storage element 152 and the acceptance element 150, in at least a portion of the crotch region 37 of the article. However, as noted above if the storage element 152 has transportation capabilities, the immobilization element 154 may be located anywhere in the diaper 20 such that the viscous fluid bodily waste accepted and/or stored can be transported to the immobilization element 154. Further, as with the acceptance and storage elements 150 and 152, the diaper 20 may have uniform or non-uniform Immobilization Under Compressed Inversion performance characteristics. Thus, one or more immobilization elements 154 may incorporated in the article having regions of different immobilization and/or retention performance. Further, any or all of the immobilization element 154 may be removable from the absorbent article for separate disposal, if desirable.

Suitable materials for use in the immobilization element 154 include microporous foams, superabsorbent polymer particles or fibers, cellulosic fibers, capillary channel fibers, entangled synthetic fiber batts and the like. Some preferred materials include foam absorbent materials such as those described in U.S. Pat. Nos. 5,260,345; 5,387,207; and 5,650,222. Other preferred materials include absorbent gelling materials such as those described in U.S. Pat. No. 5,147,345 entitled "High Efficiency Absorbent Articles For Incontinence Management" issued to Young et al. on Sep. 15, 1992. Each of these patents is hereby incorporated by reference herein.

Data on several individual immobilization elements are provided in Table V. The test for Immobilization Under Compressed Inversion performance of an individual immobilization element 154 is the same as the Immobilization Under Compressed Inversion test method described below relating to structures configured as intended for use, except that it is performed only on the individual storage element 152 and/or immobilization element 154, and does not include overlying elements such as topsheets or acceptance elements. Further, the sample is tested with the standard acceptance element 151 described above. (Analog B, as described below, is used as the test analog.)

TABLE V

Immobilization Under Compressed Inversion Using a Standard Acceptance Element

| Storage Element | Storage Under Pressure (g/in$^2$) | Immobilization Under Compressed Inversion (%) |
|---|---|---|
| Acquisition Layer from Pampers Premium Size 5 Diaper available from Procter & Gamble, Cinti., OH | 0.45 | 91 |
| Loop landing element of Comparative Example 5 without apertured vacuum-formed film topsheet | 0.52 | 71 |
| Large-cell formed film of Comparative Example 3 without hydroentangled apertured nonwoven web topsheet | 0.70 | 66 |
| Scrubber particles of Example 3 without woven netting topsheet | 1.14 | 70 |
| Mixture of scrubber particles and foam strips of Example 5 without woven netting topsheet | 1.80 | 81 |
| Layered assembly of scrubber particles and foam strips of Example 6 without woven netting topsheet | 1.89 | 78 |

Preferred Embodiments

As noted above, the present invention is applicable to many types of absorbent articles such as diapers, training pants, incontinence briefs, incontinence undergarments or pads, absorbent inserts, diaper holders and liners, feminine hygiene garments, wipes, disposable mops, bandages and the like. Thus, the following examples of preferred embodiments of the present invention should not be construed to limit the scope of the invention.

One preferred embodiment of the present invention is the absorbent article 20A illustrated in FIGS. 5, 6 and/or 6A. The absorbent article 20A has a first waist region 36, a second waist region 38 and a crotch region 37 located between the first waist region 36 and the second waist region 38. The diaper 20A includes a topsheet 24, a backsheet 26 and an absorbent core 28 disposed between the topsheet 24 and the backsheet 26. The topsheet 24 is disposed in at least a portion of the first waist region 36 adjacent the body facing surface 47 of the core 28. The diaper 20A also includes an acceptance element 150 joined with the topsheet 24 and extending longitudinally away from the topsheet 24 through at least a portion of the crotch region 37 and at least a portion of the second waist region 38. The acceptance element 150 includes a woven netting available as a Tub Toy Bag from Dollar Tree Dist., of Norfolk, Va.

The diaper 20A further includes a storage element 152 located between the acceptance element 150 and the backsheet 26. The storage element 152 is located in at least a portion of the crotch region 37 and at least a portion of the second waist region 38. In this embodiment, the storage element 152 includes a macro-particulate structure 170 comprising particles 172. Specifically, the macro-particulate structure 170 includes about two grams of the scrubber particles from Example 4, below, mixed with about 0.35 grams of strips of foam absorbent material having a basis weight of 45 grams per square meter, as described in U.S. Pat. No. 5,260,345. The strips have dimensions of about 19 millimeters in length, 6.4 millimeters in width, and 2 millimeters in thickness. The scrubber particles are distributed over a 2.5 inch×6.4 inch (16 square inch) area disposed along the longitudinal axis of the article of approximately 0.8 mm thick "thin until wet" foam absorbent material (described in U.S. Pat. No. 5,387,207 which is incorporated herein by reference) having a basis weight of 126 grams per square meter. The scrubber particles are relatively homogeneously mixed with the absorbent foam strips and are free to move within the area circumscribed by the layer of "thin-until-wet" absorbent foam material. The particles and strips are preferably not bonded to the woven netting topsheet or any other layer. The acceptance element 150 is bonded to the underlying layers outside the periphery of the layer of "thin-until-wet" absorbent foam.

Figure 8:
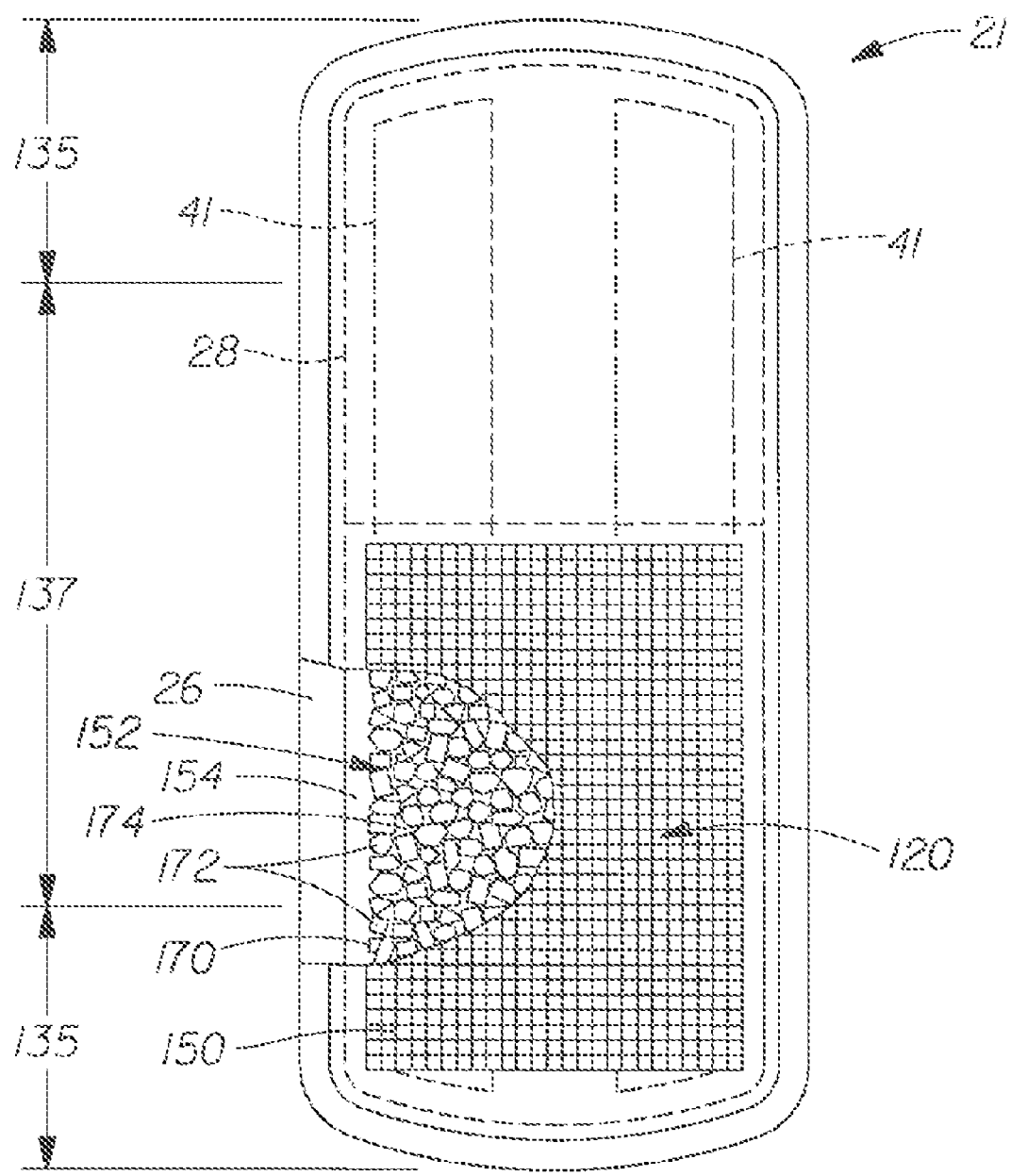
FIG. 8 is a plan view of an alternative embodiment of the present invention.

In another embodiment, as shown in FIG. 8, the absorbent article of the present invention may be an insert 21 or sanitary napkin which is intended to be applied separately to the wearer or to be placed in the wearer's underwear, an outer cover or the like. Thus, the insert 21 is generally not intended to take the form of a pant, but rather is to be used in conjunction with a pant or other structure which holds the insert 21 in place about the wearer. The absorbent insert 21 has a pair of opposed end regions 135 separated by a central region 137 and includes an absorbent assembly 27 which may include an absorbent core 28, an acceptance element 150, a storage element 152 and/or an immobilization element 154. The insert 21 may also include one or more attachment element(s) 41 to hold the insert 21 in place in the pant or outer cover 29 during use. The attachment element 41 may comprise adhesive, cohesive, hooks, snaps, buckles, buttons, ties, magnetic, electronic and/or any other know means for attaching absorbent articles to undergarments.

Test Methods

Viscosity

The viscosity may be determined by a controlled stress rheometer. A suitable rheometer is available from T. A. Instruments, Inc. of New Castle, Del., as model number SC$^2$100. The rheometer utilizes a stainless steel parallel plate fixture. The rheometer has a rigid horizontal first plate onto which the sample is placed and a second plate mounted over the first plate such that the axis of said second plate is perpendicular to the first plate. The second plate is 2 or 4 centimeters in diameter. A two centimeter (2 cm) parallel plate is used for firm, pasty, or highly mucousy samples, while the four centimeter (4 cm) parallel plate is used for very runny or "water-like" fecal samples. The first and second plates are spaced apart up to 2000 microns during the measurement process. The second plate is connected to a drive shaft for axial rotation. The drive motor and strain sensor are also mounted on the drive shaft.

A suitable sample (typically 2 to 3 grams) of an analog to be tested is centered on the first plate and generally centered beneath the axis of the second plate. Prior to the test, any large pieces of undigested food material (e.g., seeds) are removed. The first plate is raised into position. Excess amounts of the sample which are displaced beyond the diameter of the second plate are removed using a spatula. Water is then misted around the edges of the sample to prevent edge effects due to moisture loss during the measurement process. A programmed application of a shear stress, from 50 to 50,000 dynes/cm$^2$ for pasty and firm samples, is applied to the sample by the rheometer. For runny and watery samples, a shear stress range of 5 to 5000 dynes/cm$^2$ was used instead. The data is fitted to a power law function where the apparent viscosity=$kj^{(n-1)}$, k=consistency (units of cP×sec$^{(n-1)}$), j=shear rate (Units of 1/sec), and n=shear index (dimensionless). Therefore, when j=one 1/sec, the viscosity=the value of k (units of cP). (The plates are maintained at 35 degrees C. throughout the test.)

Acceptance and Receptivity Under Pressure

Figure 2:
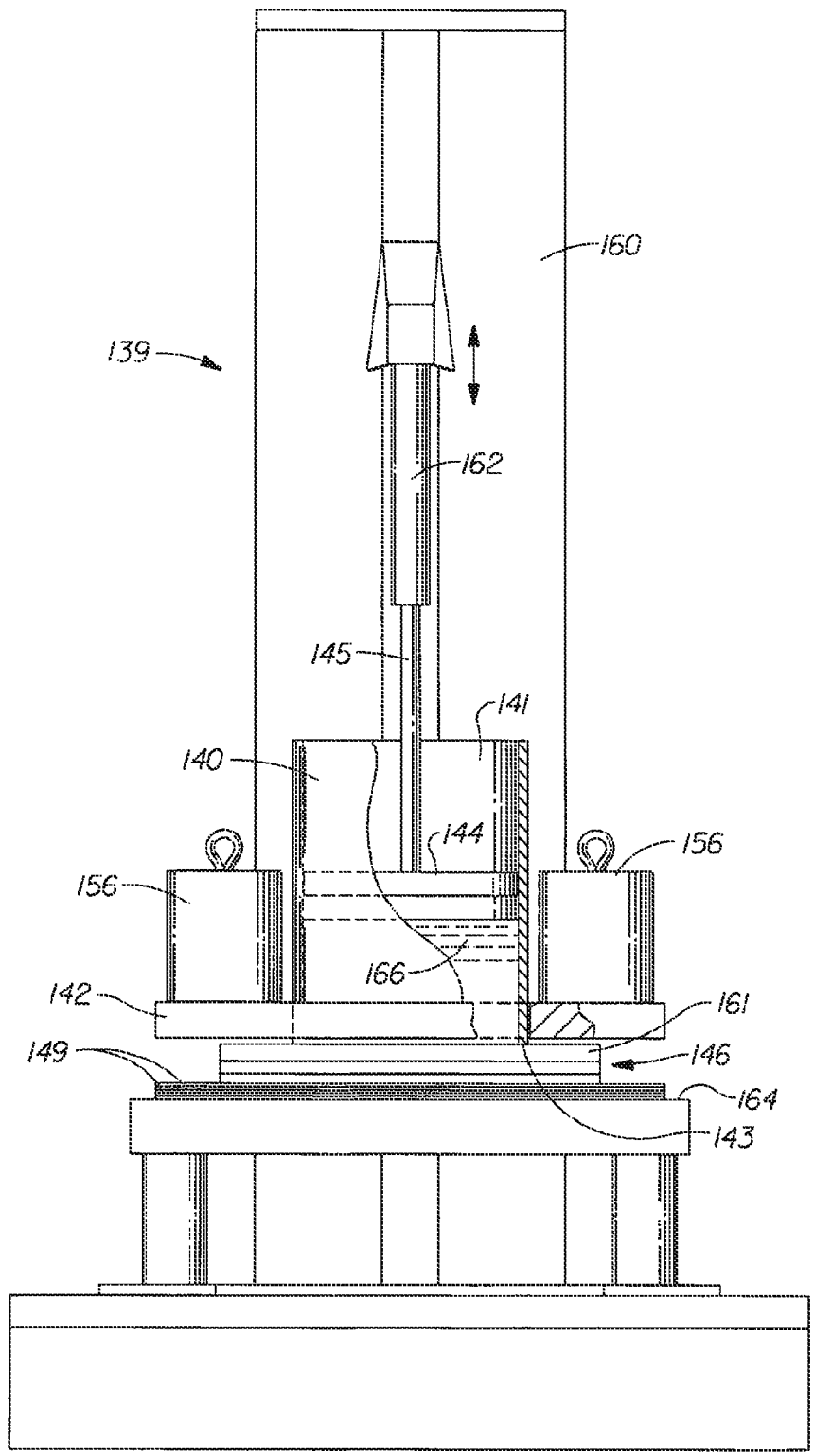
FIG. 2 is a schematic front and cutaway view of an apparatus which may be used to measure Acceptance Under Pressure and Storage Under Pressure characteristics of structures.
Figure 3:
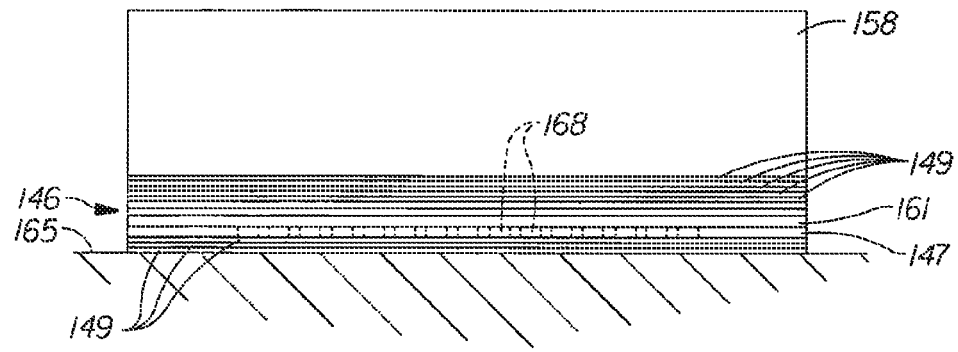
FIG. 3 is a schematic side view of an apparatus which may be used to measure retention and Immobilization Under Compressed Inversion characteristics of structures.

Acceptance Under Pressure is measured by the following test which uses the apparatus 139 illustrated in FIG. 2. A hollow plexiglass cylinder 140 is provided mounted on a stainless steel plate 142 about 9.5 mm thick. The plate 142 is a square, about 10.16 cm×10.16 cm (about 4 in.×4 in.). The cylinder 140 and plate combination has a height of 7.6 centimeters (about 3.0 inches), an inside diameter of 5.08 centimeters (about 2.00 inches) and an outside diameter of 6.3 centimeters (about 2.48 inches). The bottom of the cylinder 140 extends below the plate 142 a distance of about 3.5 millimeters. The lip 143 prevents the test fluid 166 from leaking outside the designated test area. Two 625 gram weights 156 are also provided, each having a diameter of 5.08 cm (about 2.0 inches).

A cylindrically shaped 24.6 gram plexiglass weight 144 is provided. The weight 144 has a diameter of 5.08 centimeters (about 2.0 inches), so that the weight 144 fits with close tolerance within the cylinder 140 but can freely slide throughout the hole 141 in the cylinder 140. This arrangement provides a pressure of about 119 Pascals (Pa) (about 0.017 pounds per square inch) and a test area of about 20.27 square cm (about 3.142 square inches). If desired, the weight 144 may have a handle 145 to allow it to be easily inserted into and removed from the cylinder 140. In such cases, the combined mass of the handle 145 and the cylindrical weight 144 should equal 24.6 grams.

A sample 146 of the structure to be tested for Acceptance Under Pressure properties is provided. The sample 146 may be cut from an existing diaper or may be constructed from material which has not been formed into a diaper. The sample 146 includes the entire structure intended for use in an article or the entire structure of the article to be evaluated, including the top layer 161. (In order to measure the Acceptance Under Pressure performance of discrete acceptance elements, as described in the Acceptance Element section above, the Acceptance Under Pressure test is performed using the standard storage element 147 in place of any underlying structure or layers.) The sample 146 should be cut into a square measuring 10.16 centimeters by 10.16 centimeters (about 4 inches by 4 inches).

Five layers of a high basis weight blotter 149 measuring 4 inches×4 inches are provided. The top layer 161 of the sample 146 is removed and the remaining components, or layers, of the sample 146 (if there are multiple components or layers) and the five sheets of blotter material 149 are weighed to the nearest 0.01 grams. Thus, if the sample 146 is being taken from a diaper, the layers of the diaper such as topsheets, secondary topsheets, acquisition layers, absorbent cores etc., should be separated prior to weighing. (In some cases, a single layer may comprise two or more permanently bonded components.) In so doing, care must be taken not to destroy the sample 146 or cause unintended gross deformation of any parts of the sample 146. The layers of the sample 146 may be frozen to aid their separation from adjacent layers of the sample 146. Freezing may be accomplished using PH100-15 circuit refrigerant made by Philips ECG, Inc. of Waltham, Mass.

The sample 146 should be reassembled as originally configured on top of 5 stacked layers of blotter material 149 with the side of the sample 146 intended to face the wearer oriented facing up and away from the blotter material 149. The blotter material 149 is preferably filtration grade paper, available from Ahlstrom Filtration, Inc. of Mt. Holly Springs, Pa. as #632-025, having a basis weight of about 90 grams per meter.

The combined assembly of the sample 146 and the blotter material 149 is centered on the work surface 164 of a Stevens-Farnell QTS-25 Model 7113-5 kg Texture Analyzer 160 (available from Leonard Farnell Co. of Hatfield, England), under the probe 162. A suitable probe 162 is a 100 cm flat-ended cylindrical aluminum extension rod QTSM3100 available from the Leonard Farnell Co. of Hatfield England. The cylinder 140 is centered on the sample 146. The two 625 gram weights 156 are placed on opposite corners (diagonally) of the plate 142 to stabilize it. A syringe having an opening of about 4 to 6 millimeters is used to dispense approximately 10 cubic centimeters of viscous fluid bodily waste analog 166 (Analog A as described below) through the hole 141 in the cylinder 140 onto the top of the sample 146.

Viscous fluid bodily waste analog, Analog A, is a fecal material analog made by mixing 10 grams of CARBOPOL 941 available from the B.F. Goodrich Corporation of Brecksville, Ohio, or an equivalent acrylic polymer in 900 milliliters of distilled water. The CARBOPOL 941 and distilled water are weighed and measured separately. A 3-bladed marine-type propeller having a 2 inch diameter paddle, (available from VWR Scientific Products Corp. of Cincinnati, Ohio, Catalog #BR4553-64, affixed to a ⅜" stirring shaft BR4553-52), is used to stir the distilled water. The propeller speed should be constant at 450 rpm during mixing. The mixer should form a vortex without splashing. The CARBOPOL is slowly sieved into the water so that it is drawn into the vortex and mixed without forming white clumps, or "fish eyes". The mixture is stirred until all of the CARBOPOL has been added, and then for a period of 2 minutes thereafter. The sides of the bowl containing the mixture should be scraped and the bowl should be rotated as needed to achieve a homogeneous mixture. (The mixture will likely be slightly cloudy with air bubbles). One hundred grams of a 1.0 N volumetric NaOH solution, available from J. T. Baker Co., Phillipsburg, N.J., is then slowly measured into the mixture and the mixture is stirred until homogeneous. The mixture should become thick and clear. The mixture should be stirred for 2 minutes after the addition of the alkali solution. The neutralized mixture should be allowed to equilibrate for at least 12 hours and should be used for the Acceptance Under Pressure test within 96 hours thereafter. Before the CARBOPOL mixture is used, it should be stirred in the container at low speed (about 50 rpm) for about 1 minute to ensure the mixture is homogeneous.

Analog A should, if prepared correctly, have a "hardness" value between 55 and 65 grams. Hardness is measured using a Stevens-Farnell QTS-25 Texture Analyzer, model 7113-5 kg, and associated software on an Intel-based machine having a 486 processor or higher. A ½ inch stainless steel spherical probe and an analog receptacle are provided. A suitable probe is the TA18 probe available from Leonard Farnell Co. of Hatfield, England. The analog receptacle can be made by cutting a 7 milliliter linear low density polyethylene scintillation vial (having an inside diameter of 0.55 inches+/−0.005 inches) to a 15 millimeter length. Suitable vials are available from Kimble Glass Company of Vineland, N.J. as #58503-7 vials. The analog receptacle is filled to within 2 millimeters of the top edge with the analog to be tested. The vial is centered under the ½ inch spherical stainless steel probe. The probe is lowered to a distance of about 1 millimeter from the surface of the analog in the vial. The probe 162 is moved downward 7 millimeters at 100 millimeters per minute and then stopped. The Hardness is the maximum recorded resistive force encountered by the probe on its 7 millimeter stroke. (The temperature of the room and the analog should be between about 65 to 75 degrees Fahrenheit during the course of the measurement.)

Once the proper amount of viscous fluid bodily waste analog 166, Analog A, has been measured into the cylinder 140, the 24.6 gram weight 144 is inserted slowly and gently into the hole 140 in the cylinder 140 until it rests on the surface of the analog. The Texture Analyzer 160 is activated so the probe 162 depresses the cylindrical weight 144 at a rate of 10 millimeters per minute until a resisting force of about 144.6 grams is reached. The Texture Analyzer 160 is set to stop the downward stroke once the resistance force of 144.6 grams is reached. The recorder is set to trigger at a resistive force of 5 grams. (The maximum resisting force of 144.6 grams corresponds to an applied pressure of 700 Pascals or 0.1 pounds per square inch). Once a resistive force of 144.6 grams is reached, the probe 162 is retracted to its starting position.

The weight 144 is removed from the cylinder 140, and then the cylinder 140 is removed from the surface of the sample 146, taking care not to drip any Analog A remaining in the cylinder 140 onto the sample. The top layer 161 of the sample 146 is then removed from the underlying layer(s) of the sample 146 by dragging the top layer 161 parallel to the surface of the underlying layers, if possible. For certain structures where the top layer 161 is difficult to remove by dragging parallel to the underlying layers, the top layer 161 may be peeled or lifted away from the underlying layers of sample 146. If the sample 146 comprises only a single layer, the standard acceptance element 151, described below, is utilized as the top layer 161 of the sample 146. The underlying layers of the sample 146 and the blotter material 149 are then weighed. The amount of test Analog A accepted by the sample 146 equals the increase in combined weight of the underlying layer(s) of the sample 146 and the blotter material 149 caused by the test Analog A penetrating through the top surface layer of the sample 146 per unit work performed (in millijoules) on a unit area basis. The area under the force vs. distance curve, used in calculating the unit work, is calculated by integrating the force resisting the probe on its downward stroke over the total distance traveled until the maximum force of 144.6 grams is registered. The unit work is calculated using the following equation:

$$\text{Unit Work(mJ)} = \text{Area under the force vs. distance curve(g/mm)}(9.81 \text{ m/s}^2)/(1000 \text{ mm/m})$$

Receptivity Under Pressure is measure in the same manner as Acceptance Under Pressure, as described above, except that the time required to reach the resistive force of 144.6 grams on the downward stroke of the probe 162 is measured and recorded. Receptivity Under Pressure is calculated using the following equation:

$$\text{Receptivity Under Pressure (g/in}^2\text{/mW)} = \frac{\text{Acceptance Under Load (g/in}^2\text{/mJ)}}{\text{Time required to Reach 144.6 g Resistive force (sec)}}$$

Storage Under Pressure

Storage Under Pressure is measured using the same apparatus 139 described above and illustrated in FIG. 2. The hollow cylinder 140, weight 144, and 625 g weights 156 described in the Acceptance Under Pressure test above are provided. A sample 146 of the structure to be tested for Storage Under Pressure properties is also provided. Again, the sample 146 may be cut from an existing diaper 20 or may be constructed from material which has not been formed into a diaper. The sample 146 should include the entire structure intended for use in an article or the entire structure of the article to be evaluated. (In order to measure the Storage Under Pressure performance of discrete storage elements, as described in the Storage Element section above, the Storage Under Pressure test is performed using the standard acceptance element 150 in place of any overlying structure or layers.) The sample 146 should be cut into a square measuring 10.16 centimeters by 10.16 centimeters (about 4 inches by 4 inches).

Five layers of a high basis weight blotter 149 (identical to that described in the Acceptance Under Pressure test above) measuring 4 inches×4 inches are provided. The top layer 161 of the sample 149 is removed and the remaining components, or layers, of the sample 146 (if there are multiple components or layers) and the five sheets of blotter material 149 are weighed to the nearest 0.01 grams. Thus, if the sample 146 is being taken from a diaper, the top layer 161 of the diaper, such as the topsheet 25, should be separated from the sample 146 prior to weighing. In so doing, care should be taken not to destroy the sample 146 or cause unintended gross deformation of the elements of sample 146. The layers of the sample 146 may be frozen, as described above, to aid their separation from adjacent layers of the sample 146.

The sample 146 should be reassembled as originally configured on top of five stacked sheets of blotter material 149 with the side intended to face the wearer oriented facing up and away from the blotter material 149. The combined assembly of the sample 146 and the blotter material 149 is centered on the work surface 164 of the Texture Analyzer 160 (described above), under the probe 162. The cylinder 140 is centered on the sample 146. The two 625 gram weights 156 are placed on diagonally opposite corners of the plate 142 to stabilize it. A syringe having an opening of about 4 to 6 millimeters is used to dispense 10 cubic centimeters Analog A (as described above) through the hole in the cylinder 140 onto the top of the sample 146. The 24.6 gram weight 144 is inserted into the hole 141 in the cylinder 140 and the Texture Analyzer 160 is activated with the probe 162 depressing the cylindrical weight 144 at a rate of 10 millimeters per minute until a resisting force of 144.6 grams is reached. (The maximum resisting force of 144.6 grams corresponds to an applied pressure of 700 Pascals or 0.1 pounds per square inch). Once the resisting force of 144.6 grams is reached, the probe 162 is retracted to its starting position.

The weight 144 is removed from the cylinder 140, and then the cylinder 140 and weights 156, are removed from the surface of the sample 146, taking care not to drip any Analog A remaining in the cylinder 140 onto the sample. The sample 146 is then removed from the work surface 164 of the Texture Analyzer 160 by dragging the sample 146 parallel to the work surface 164, if possible. For certain structures where the top layer 161 is difficult to remove by dragging parallel to the underlying layers, the top layer 161 may be peeled or lifted away from the underlying layers of sample 146. The sample 146 and the blotter 149 are then weighed. The amount of test Analog A 166 stored equals the increase in combined weight of the underlying layers of the sample 146 and the blotter 149 caused by the test Analog A penetrating into the sample 146 on a unit area basis.

Immobilization and Retention Under Compressed Inversion

To measure Immobilization Under Compressed Inversion and Retention Under Compressed Inversion, a cylinder 140 is mounted on plate 142. The cylinder 140 has a height of 7.5 centimeters (about 2.95 inches), an inside diameter of 5.08 centimeters (about 2.00 inches) and an outside diameter of 6.3 centimeters (about 2.48 inches). The hollow cylinder 140 and plate 142 are identical to those used in the Acceptance Under Pressure and Storage Under Pressure tests described above, with the exception that the plate does not have the "lip" 143 on the bottom, and that both the cylinder 140 and the plate 142 are made of stainless steel. The stainless steel cylinder 140 and plate 142 have a combined weight of about 1170 grams.

The sample 146 of the structure to be tested is provided and the top layer 161, if included in the sample 146, is removed. The remaining underlying layers of the sample 146 and the five layers of blotter material 149 are assembled and weighed. The top layer 161 is then placed on top of this assembly. The sample 146 may also be made from materials that have not been made into a structure. The combined assembly of the sample 146 to be tested and blotter 149 is placed on a bench top 165. (In order to measure the Immobilization Under Compressed Inversion and Retention Under Compressed Inversion performance of discrete immobilization and retention elements, as described in the Immobilization Element section above, the Immobilization Under Compressed Inversion test is performed using the standard acceptance element 150 in place of any top layer 161. All underlying layers are included in this evaluation.) A syringe having an opening of about 4 to 6 millimeters is used to dispense 10 cubic centimeters of test analog through the hole in the cylinder 40 onto the top of the sample 146. The test analog (Analog B) used in this measurement is an aqueous polyacrylamide solution prepared as follows. Twenty-two and five-tenths (22.5 g) grams of polyacrylamide, available from Aldrich Chemical Company of Milwaukee, Wis. is mixed with a solution of 20 g of Dawn dishwashing solution, available from the Procter & Gamble Company of Cincinnati, Ohio, diluted with 1000 ml distilled water. Mixing is done using the same propeller used in mixing Analog A, except that the propeller speed should be constant during mixing at about 650 rpm. Mixing is done for 30 minutes in a water bath at 180° F. The heated water bath is removed and the mixture is stirred for an additional 30 minutes. The mixture is allowed to equilibrate for at least 12 hours and used for the Immobilization Under Compressed Inversion test within 96 hours. Analog B should have a hardness value (measured as described above for Analog A) of between about 7.5 and about 10.5 grams. Analog B is designed to simulate the water suction power of actual runny feces from breastfed babies. Analog B is generally easier to accept (i.e., more mobile) than Analog A, which makes its retention more difficult.

The test analog (Analog B) is allowed to penetrate the sample 146 under gravitational force for 3 minutes. The cylinder 140 is then removed from the surface of the sample 146 and the entire sample 146 is weighed. The top layer 161 of the sample 146 is then removed from the underlying layers of the sample 146 by lifting the top layer 161 vertically from the surface of the underlying layers and allowing any excess Analog B to drain back into the lower layers. The assembly of the remainder of sample 146 and the blotter material 149 is then weighed. This provides a measure of the net quantity of Analog B imbibed by the structure during the loading step of this test. The sample 146 is then reassembled, including the top surface layer 161. Three layers of the 4 inch square blotter material 149 are provided and weighed. A standard storage element 147 is provided and placed on top of the three layers of blotter material 149. The reassembled sample 146 is inverted onto the assembly of the standard storage element 147 and the three layers of blotter material 149. (The standard storage element 147 includes a 4 inch square 1.6 millimeter thick aluminum plate having a pattern of 153 regularly spaced 4.3 millimeter diameter holes 168, as shown in FIG. 4. The holes are arranged such that there are approximately 26 holes per square inch.)

A 16 pound, 16 square inch weight 158 (corresponding to a 7000 Pascal pressure, or 1.0 psi) is then gently placed on the surface of the sample 146 which is facing away from the standard storage element 147. The weight 158 is removed after three minutes, and the sample 146 is reoriented so that the side insulted by the test Analog B is facing up. The top layer 161 is removed and the weight of the remaining layers of sample 146 and the five layers of blotter material are measured and recorded. The sample's Retention Under Compressed Inversion is calculated as the actual net amount of test Analog B present in the underlying layers of the structure after the inversion cycle.

Immobilization Under Compressed Inversion is calculated as the percentage of the test Analog B that penetrated the structure (i.e., passed through the surface layer into the underlying layers of the sample) during the loading step which remains in the underlying layers of the structure after the inversion step. The equation for determining Immobilization Under Compressed Inversion is as follows:

$$\text{Immobilization Under Compressed Inversion} = \frac{\text{Retention Under Compressed Inversion (g)}}{\text{Net Quantity of Analog } B(g) \text{ imbibed during loading step}} \times 100\%$$

Compressive Resistance and Void Volume

The compressive resistance and void volume of storage elements can be calculated from the measurement of the storage element basis weight and caliper under compression. These physical properties are important to understand the maximum absorption capacities at different compression pressures.

A 2.25 inch diameter circular sample of the structure to be tested is punched out using a die cutter. The weight of the sample is measured using an analytical balance and recorded in grams. The sample basis weight (in grams per square meter) is calculated by dividing the weight of the sample in grams by the surface area of the sample in square meters.

With a digital caliper gauge (Model # EG-225 manufactured by Ono Sokki caliper measurements at 0.09, 0.2, 0.5, 1.0 and then again at 0.09 psi are measured and recorded in sequence. (This gauge has a lip upon which slotted weights can be mounted. This lip by itself (i.e., with no additional weights) exerts a baseline force of 0.07 psi when resting on the sample.) A 30 second waiting period is required between readings. It is important to note that the same sample should be used to measure calipers at all compression forces. The sample should also be fixed in one position and all caliper readings should taken at the same location on the sample. The change from one compression force to another should be done within 5-10 seconds by changing out the weights quickly.

At each compression force, void volume and compressive resistance are calculated as follows:

$$\text{Bulk Density (g/cc)} = \frac{\text{Weight of structure/solid (g)}}{\text{Total (fluid + solid) volume}} \text{(Fluid = liquid and/or air)}$$

$$\text{Bulk Density (g/cc)} = \frac{\text{Basis Weight (g/m}^2\text{)}}{\text{Caliper (cm)}} \times 10^{-4}$$

$$\text{Intrinsic density (g/cc)} = \frac{\text{Weight of solid (g)}}{\text{Volume of the solid (cc)}}$$

$$\text{Porosity} = \frac{1 - \text{Bulk density (g/cc)}}{\text{Intrinsic Density (g/cc)}}$$

$$\text{Void Volume (cc/g)} = \frac{1}{\text{Bulk Density (g/cc)}} - \frac{1}{\text{Intrinsic density (g/cc)}}$$

Compressive Resistance, as used herein, is the ratio of the caliper of the structure measured under the 0.2 psi pressure and the caliper at 0.07 psi (i.e., the caliper when the unloaded lip of the caliper gauge is resting on the sample). The equation to calculate Compressive Resistance is shown below.

$$\text{Compressive Resistance (\%)@0.2 psi} = \frac{\text{Caliper at 0.2 psi (cm)}}{\text{Caliper at 0.07 psi (cm)}} * 100$$

Resiliency is the ratio of the caliper of the structure measured at 0.07 psi after the entire compression cycle is complete (i.e., after the structure has been subjected to increasing pressures from 0.07 psi through 1 psi as described above) and divided by the initial caliper at 0.07 psi before the compression loading cycle.

$$\text{Resiliency (\%)} = \frac{\text{Caliper at 0.07 psi after the complete compression cycle (0.07 - 1 psi)} * 100}{\text{Caliper at 0.07 psi before the compression loading cycle}}$$

EXAMPLES

Comparative Examples 1-5 are comparative examples of combination structures known in art. Examples 1-17 are illustrative embodiments of the present invention. Each of the structures was tested as described above to determine its capacity to accept, store, immobilize and retain viscous fluid bodily waste. The results are plotted on the graphs shown in FIGS. 9-22.

Comparative Example 1

A four inch by four inch (4 in.×4 in.) sample cut from a Size 1 PAMPERS Premium diaper, available from the Procter & Gamble Co., Cincinnati, Ohio. The sample comprises all the layers of the product and is taken from the region containing the rearmost four inches of the absorbent core. The nonwoven topsheet is separated from the underlying layers for weighing prior to testing as described above. All of the layers are included in the actual test.

Comparative Example 2

Figure 7:
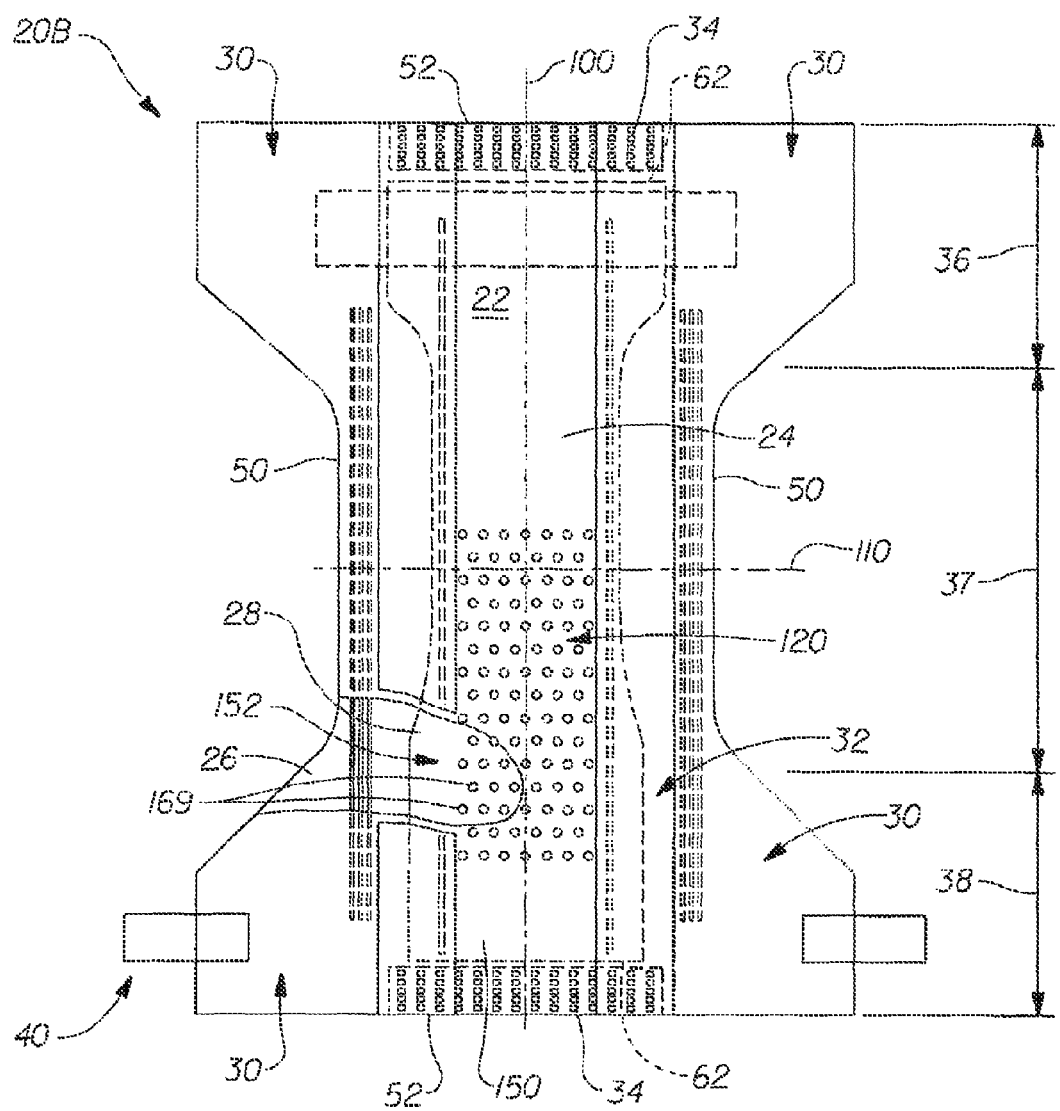
FIG. 7 is a plan view of one embodiment of the present invention having portions cut away to reveal the underlying structure, the body facing surface of the diaper facing the viewer.

A four inch by four inch (4 in.×4 in.) sample cut from a Size 1 PAMPERS Premium diaper, available from the Procter & Gamble Co., Cincinnati, Ohio. The sample comprises all the layers of the product and is taken from the crotch region area containing the absorbent core. Eight millimeter diameter holes are punched though the structure of a diaper 20B, spaced 13 millimeters on center in staggered rows (see FIG. 7). The topsheet is not removed from the structure prior to punching the holes. An apertured vacuum-formed film available as X-3265 from Tredegar Corporation of Terre Haute, Ind. is placed over this structure as a topsheet for testing.

Comparative Example 3

A hydroentangled apertured nonwoven web, available as GH437 from the Chicopee, Inc. of North Charleston, S.C., is placed over a large-cell vacuum-formed film available from Tredegar Corporation of Terre Haute, Ind. as X5790.

Comparative Example 4

An apertured vacuum-formed film available as X-3265 from Tredegar Corporation of Terre Haute, Ind. is placed over a 6 denier polyester crimped and resin-bonded highloft nonwoven, having a basis weight of 110 grams per square meter and an uncompressed thickness of 7.9 millimeters, available from the Glit Company of Wrens, Ga.

Comparative Example 5

An apertured vacuum-formed film available as X-3265 from Tredegar Corporation of Terre Haute, Ind. is placed over a mechanical fastening loop landing element, having an uncompressed thickness of about 1.5 millimeters available as XPL-7124 from the 3M Corporation of Minneapolis, Minn.

Example 1

A woven netting available as a Toy Tub Bag from Dollar Tree Dist., of Norfolk, Va. is placed over a 6 denier polyester crimped and resin-bonded highloft nonwoven. The nonwoven has a basis weight of 110 grams per square meter and an uncompressed thickness of 7.9 millimeters and is available from the Glit Company of Wrens, Ga. The woven netting has an effective open area of 60% and primary apertures having an effective area of 5.0 mm² (as measured by the method incorporated herein from U.S. Pat. No. 5,342,338).

Example 2

A four inch by four inch sample cut from a Size 1 PAMPERS Premium diaper, available from the Procter & Gamble Co., Cincinnati, Ohio. The sample comprises all the layers of the product and is taken from the crotch region area containing the absorbent core. Eight millimeter diameter holes are punched though the structure of the diaper 20B, spaced 13 millimeters on center in staggered rows (see FIG. 7). The topsheet is not removed from the structure prior to punching the holes. The woven netting described in Example 1, available as a Tub Toy Bag from Dollar Tree Dist., of Norfolk, Va., is placed over the structure as a topsheet for testing.

Example 3

The abrasive nonwoven highloft side (referred to hereinafter as the "scrubber" layer) of a scrubbing pad available as Light Duty Scrubbers #00065 from The Libman Company of Arcola, Ill. is separated from the sponge layer. The scrubber layer is approximately seven (7) millimeters thick. This scrubber layer is cut into particles of about 8 mm×7 mm×5 mm and spread loosely on the blotter material 149 in an approximate monolayer so as to cover an area of 16 square inches with 1.65 grams of the scrubber particles. The woven netting described in Example 1, available as a Tub Toy Bag from Dollar Tree Dist., of Norfolk, Va., is placed over the scrubber particles to form the structure to be tested.

Example 4

Two grams of the scrubber particles as described in Example 3 are mixed with 0.35 grams of strips of a foam absorbent material having a basis weight of about 45 grams per square meter (as described in U.S. Pat. No. 5,260,345 which is incorporated herein by reference). The strips have dimensions of about 19 millimeters in length, 6.4 millimeters in width, and 2 millimeters in thickness. The scrubber particles are distributed over a 16 square inch area of approximately 0.8 mm thick "thin until wet" foam absorbent material (described in U.S. Pat. No. 5,387,207 which is incorporated herein by reference) having a basis weight of 126 grams per square meter. The woven netting described in Example 1, available as a Tub Toy Bag from Dollar Tree Dist., of Norfolk, Va., is placed over the mixture to form the structure to be tested.

Example 5

1.65 grams of the scrubber particles as described in Example 3 are mixed with 0.25 grams of strips of the foam absorbent material described in Example 4. The scrubber particles and strips are distributed over a 16 square inches of the blotter material 149. The woven netting described in Example 1, available as a Tub Toy Bag from Dollar Tree Dist., of Norfolk, Va., is placed over the mixture to form the structure to be tested.

Example 6

1.65 grams of the scrubber particles as described in Example 3 is layered over 0.25 grams of the strips of foam absorbent material described in Example 4 over a 16 square inch area of the blotter material 149. The woven netting described in Example 1, available as a Tub Toy Bag from Dollar Tree Dist., of Norfolk, Va., is placed over the mixture to form the structure to be tested.

Example 7

36.35 grams (about 127 count) of 6 millimeter diameter soda-lime #3000 glass balls, available from VWR Scientific Products Corporation of Cincinnati, Ohio as Catalog #26396-621, are mixed with 0.23 grams of strips of foam absorbent material described in Example 4, each strip having length and width dimensions of about 4.5 millimeters. A four inch by four inch (4 in.×4 in.) section of Stay Put Rug Pad, available from Homemaker, 295 Fifth Street, New York, N.Y. 10016 is modified by placing a 3 inch by 3 inch (3 in.×3 in.), 6.3 millimeter high boundary, made from 25.4 millimeter wide 3M SCOTCH Masking Tape onto the pad in order to stabilize the glass balls for testing. This is in turn placed over the blotter material 149. The glass ball and foam absorbent material cube mixture are distributed within the 9 square inch area bound by the masking tape border such that a single layer of the glass beads are made. The woven netting described in Example 1, available as a Tub Toy Bag from Dollar Tree Dist., of Norfolk, Va., is placed over the mixture to form the structure to be tested.

Example 8

The standard acceptance element 150 is placed over a mechanical fastening loop landing element, having an uncompressed thickness of about 2.1 mm available as XPC-8007 from the 3M Corporation of Minneapolis, Minn.

Example 9

The standard acceptance element 150 is placed over a high denier, PET resin bonded highloft with an uncompressed thickness of about 1.7 mm available as Code 114/046/4 from the Freudenberg Company of Wienheim, Germany.

Example 10

The standard acceptance element 150 is placed over 1.65 grams of the "scrubber" particles, as described in Example 3 above, in place of the woven netting.

Example 11

The standard acceptance element 150 is placed over a needle punched polypropylene loop carpet/floor mat with an uncompressed thickness of about 7 mm produced by Royal Rubber & Manufacturing Co. of South Gate, Calif.

Example 12

The standard acceptance element 150 is placed over an open cell PU/polyester reticulated foam of uncompressed thickness of about 6.3 mm thickness and a nominal pore distribution of about 10 pores per inch (ppi) and available as SIF/10 from Foamex of Eddystone, Pa.

Example 13

The standard acceptance element 150 is placed over an open cell polyurethane/polyester reticulated foam of uncompressed thickness of about 6.3 mm thickness and a nominal pore distribution of about 10 pores per inch (ppi) and available as SIF/10 from Foamex of Eddystone, Pa. This combined structure was then placed over a layer of about 0.25 grams of the strips of foam absorbent material described in Example 4 spread loosely on the blotter material 149 in an approximate monolayer so as to cover an area of about 16 square inches to form the structure to be tested.

Example 14

The standard acceptance element 150 is placed over a layer of about 0.25 grams of the strips of foam absorbent material described in Example 4 spread loosely in approximate monolayer over the reticulated foam described in Example 13 so as to cover an area of about 16 square inches. This combined structure is placed over the blotter material 149 to form the structure to be tested.

Example 15

The standard acceptance element 150 is placed over a macroporous humidifier filter eg. Model WF1 of uncompressed thickness of about 6.6 mm manufactured by KAZ Inc. of Hudson, N.Y.

Example 16

Six denier/filament capillary channel fibers available as Code DPL-77A from Fiber Innovation Technology, Johnson City, Tenn. are needle-punched into a substrate described as DFPN162 and produced by Fiberweb, Terre Haute, Ind. to create a looped, carpet-like structure having loop diameters of approximately 8 mm, a basis weight of about 112 g/m2, and an uncompressed caliper of about 2.6 mm. The standard acceptance element 150 is placed over this needle-punched element to form the structure to be tested.

Example 17

The standard acceptance element 150 is placed over a layer of the reticulated foam described in Example 13 above. This combined structure was placed over the needle punched polypropylene loop carpet described in Example 11 to form the structure to be tested.

TABLE VI shows the Acceptance, Receptivity, and Storage Under Pressure and Immobilization and Retention Under Compressed Inversion performance of the structures which are described in Examples C1-C5 and 1-7. Various combinations of the data from TABLE V are plotted on the graphs illustrated in FIGS. 9-13.

Figure 12:
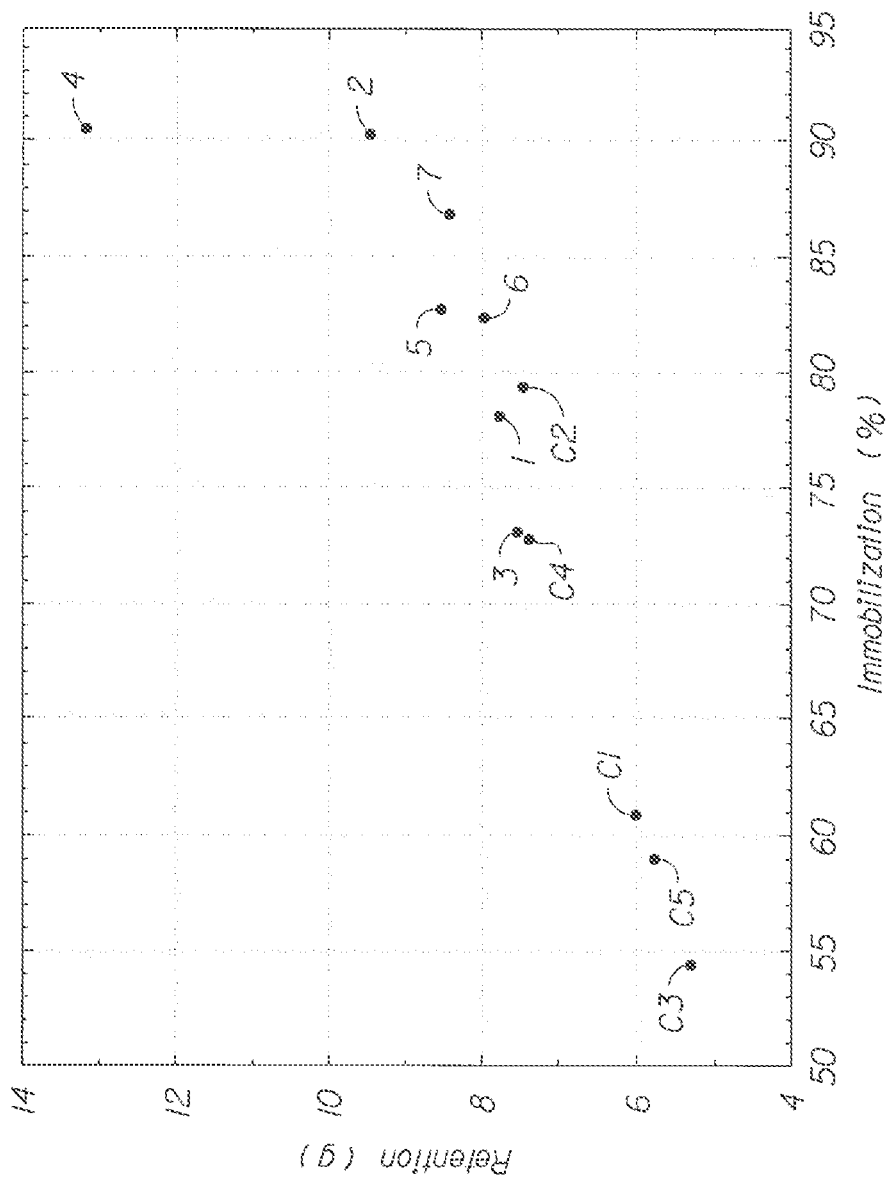
FIG. 12 is a 2-dimensional graphical representation of the relationship between retention and Immobilization Under Compressed Inversion values of exemplary structures.
Figure 13:
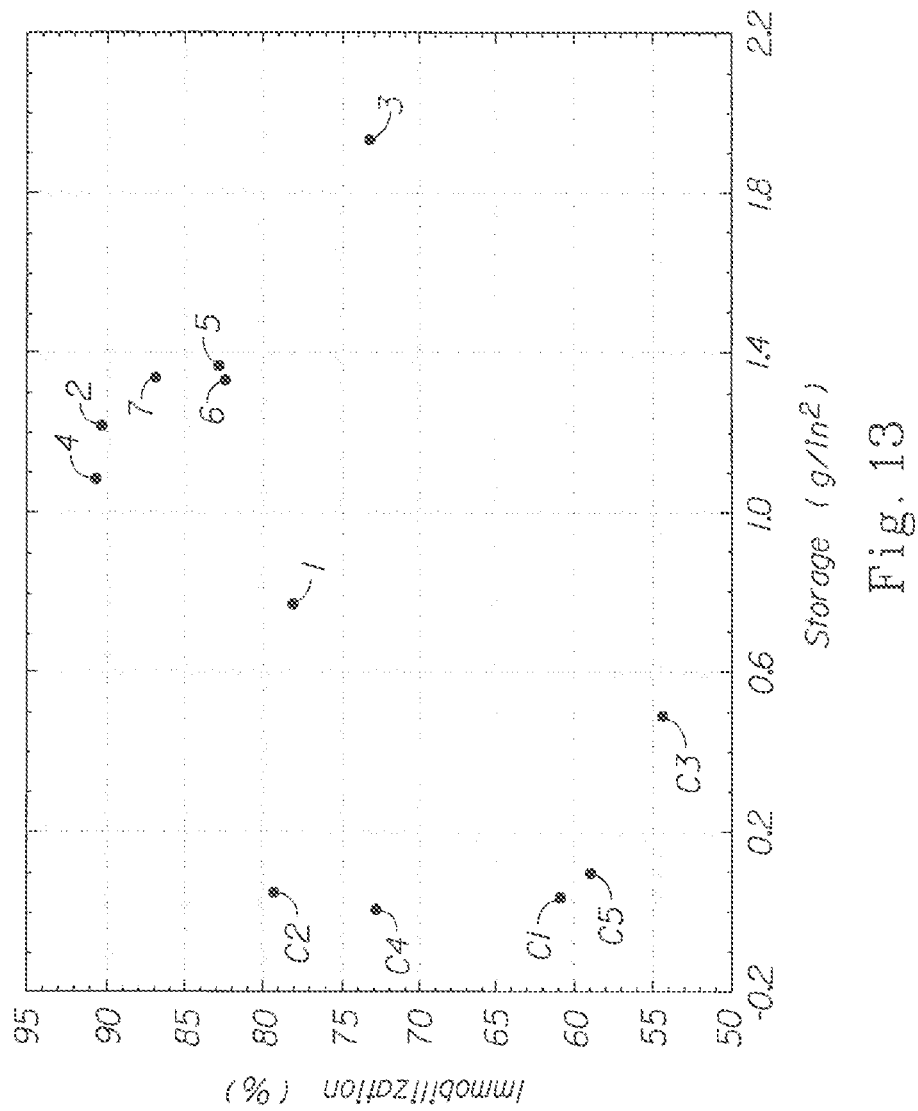
FIG. 13 is a 2-dimensional graphical representation of the relationship between Immobilization Under Compressed Inversion and Storage Under Pressure values of exemplary structures.
Figure 14:
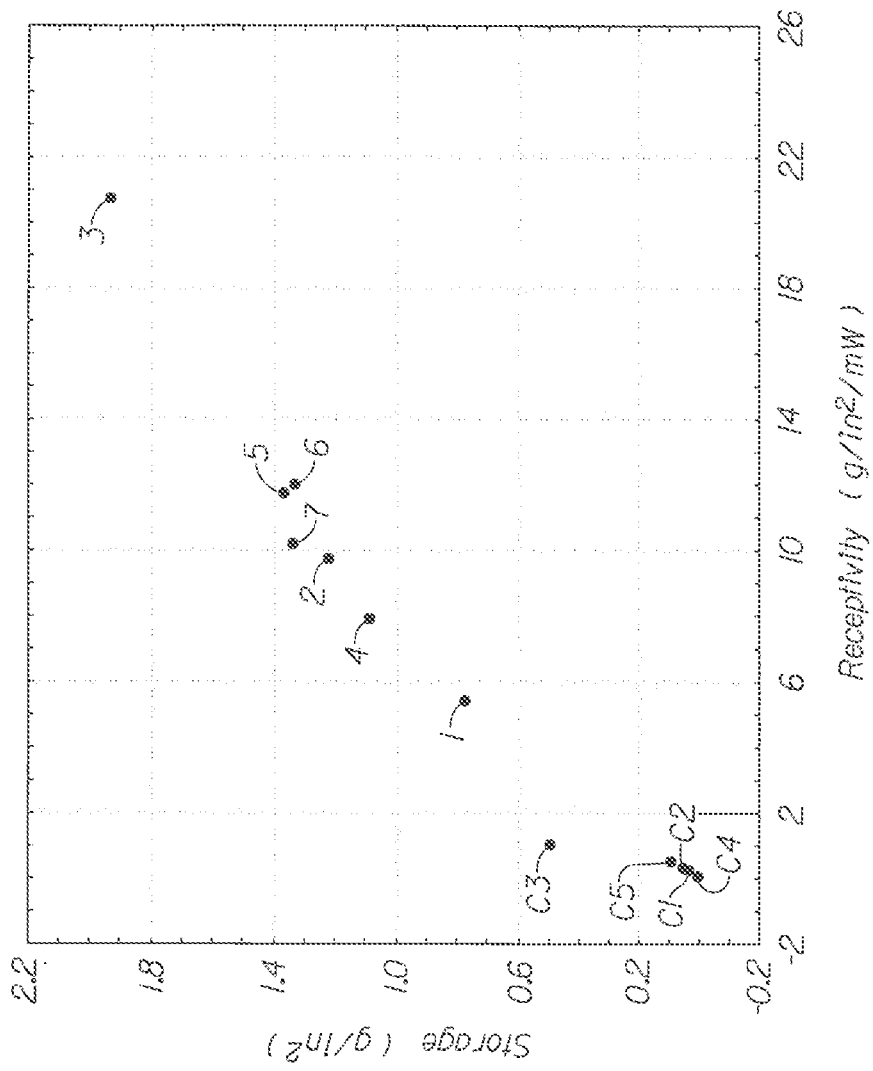
FIG. 14 is a 2-dimensional graphical representation of the relationship between Storage Under Pressure and Receptivity Under Pressure values of exemplary structures.

The importance of the combined Acceptance Under Pressure (Acceptance), Storage Under Pressure (Storage), Immobilization Under Compressed Inversion (Immobilization), and Retention Under Compressed Inversion (Retention) performance for structures intended to manage viscous fluid bodily waste is readily apparent in the graphs depicted in FIGS. 9-13. In FIGS. 9-10, the structures exemplary of the current art (Comparative Examples C1-C5) clearly occupy a different region in the three-dimensional space of Acceptance, Storage, and Immobilization shown in FIG. 9 as compared to the structures exemplary of the present invention (Examples 1-7). FIG. 9 shows the difference in Acceptance, Storage and Immobilization efficiency of the structures of the invention (Examples 1-7) in processing viscous fluid bodily waste (e.g., as is commonly excreted by 100% breastfed infants) versus the structures of the current art. This same advantage is also apparent in the three-dimensional representation of Acceptance, Storage, and Retention provided in FIG. 10. The relationship of viscous fluid bodily waste Acceptance and Storage performance for the Examples (C1-C5 and 1-7) are plotted in the graph in FIG. 11. FIG. 12 depicts the Immobilization and Retention performance of the Examples and FIG. 13 shows the relationship of Storage and Immobilization of viscous fluid bodily waste. FIG. 14 shows the relationship of Storage Under Pressure and Receptivity Under Pressure of viscous fluid bodily waste.

TABLE VII shows the Acceptance, Receptivity, and Storage Under Pressure and Immobilization and Retention Under Compressed Inversion performance of the structures which are described in Examples 8-17. Various combinations of the data from TABLE VII are plotted on the graphs illustrated in FIGS. 15-18.

TABLE VI

|  | Acceptance Under Pressure $g/in^2/mJ$ | Receptivity Under Pressure $(g/in^2/mW)$ | Storage Under Pressure $(g/in^2)$ | Immobilization Under Compressed Inversion (%) | Retention Under Compressed Inversion (g) |
|---|---|---|---|---|---|
| Comparative Examples |  |  |  |  |  |
| C1 | 0.12 | 0.25 | 0.03 | 61 | 6.0 |
| C2 | 0.13 | 0.32 | 0.05 | 79 | 7.4 |
| C3 | 0.24 | 1.03 | 0.49 | 54 | 5.3 |
| C4 | 0.01 | 0.10 | 0.003 | 73 | 7.4 |
| C5 | 0.40 | 0.52 | 0.10 | 59 | 5.8 |
| Examples |  |  |  |  |  |
| 1 | 0.92 | 5.43 | 0.77 | 78 | 7.7 |
| 2 | 0.84 | 9.77 | 1.22 | 90 | 9.4 |
| 3 | 1.27 | 20.72 | 1.93 | 73 | 7.5 |
| 4 | 1.21 | 7.93 | 1.08 | 91 | 13.1 |
| 5 | 0.82 | 11.73 | 1.37 | 83 | 8.5 |
| 6 | 0.71 | 11.99 | 1.33 | 82 | 8.0 |
| 7 | 1.18 | 10.19 | 1.34 | 87 | 8.4 |

TABLE VII

| Examples | Compressive Resistance Under 0.2 psi Pressure, % | Void Volume Under 0.2 psi Pressure, cc/in2 | Storage Under Pressure g/in2 | Acceptance Under Pressure g/in2/mJ | Receptivity Under Pressure g/in2/mW | Immobilization Under Compressed Inversion, % | Retention Under Compressed Inversion, g |
|---|---|---|---|---|---|---|---|
| 8  | 64.00 | 1.23 | 0.80 | 2.53 | 13.96 | 76.00 | 8.43 |
| 9  | 64.00 | 1.61 | 0.61 | 2.93 | 10.33 | 66.00 | 7.70 |
| 10 | 78.00 | 3.67 | 1.14 | 1.33 | 10.93 | 69.90 | 8.26 |
| 11 | 91.00 | 1.98 | 0.96 | 2.51 | 14.00 | 99.00 | 9.98 |
| 12 | 69.00 | 3.97 | 0.96 | 1.69 | 15.47 | 72.00 | 7.93 |
| 13 | 93.00 | 4.41 | 2.05 | 2.77 | 26.60 | 91.00 | 9.48 |
| 14 | 93.00 | 4.41 | 1.14 | 2.02 | 19.11 | 89.00 | 9.53 |
| 15 | 95.00 | 4.24 | 2.15 | 1.30 | 28.62 | 94.00 | 9.60 |

Figure 15:
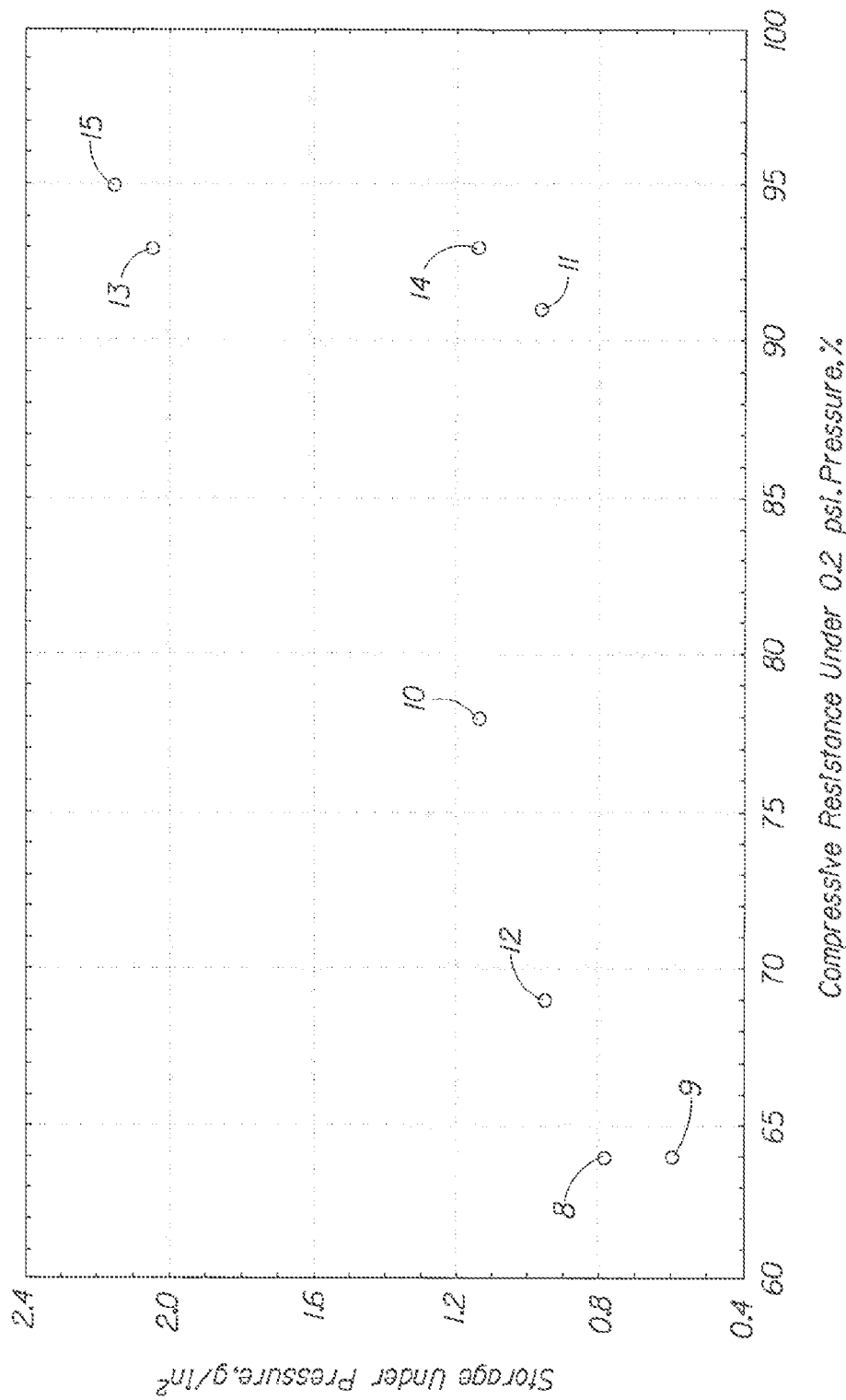
FIG. 15 is a 2-dimensional graphical representation of the relationship between Storage Under Pressure and Compressive Resistance values of exemplary structures.
Figure 16:
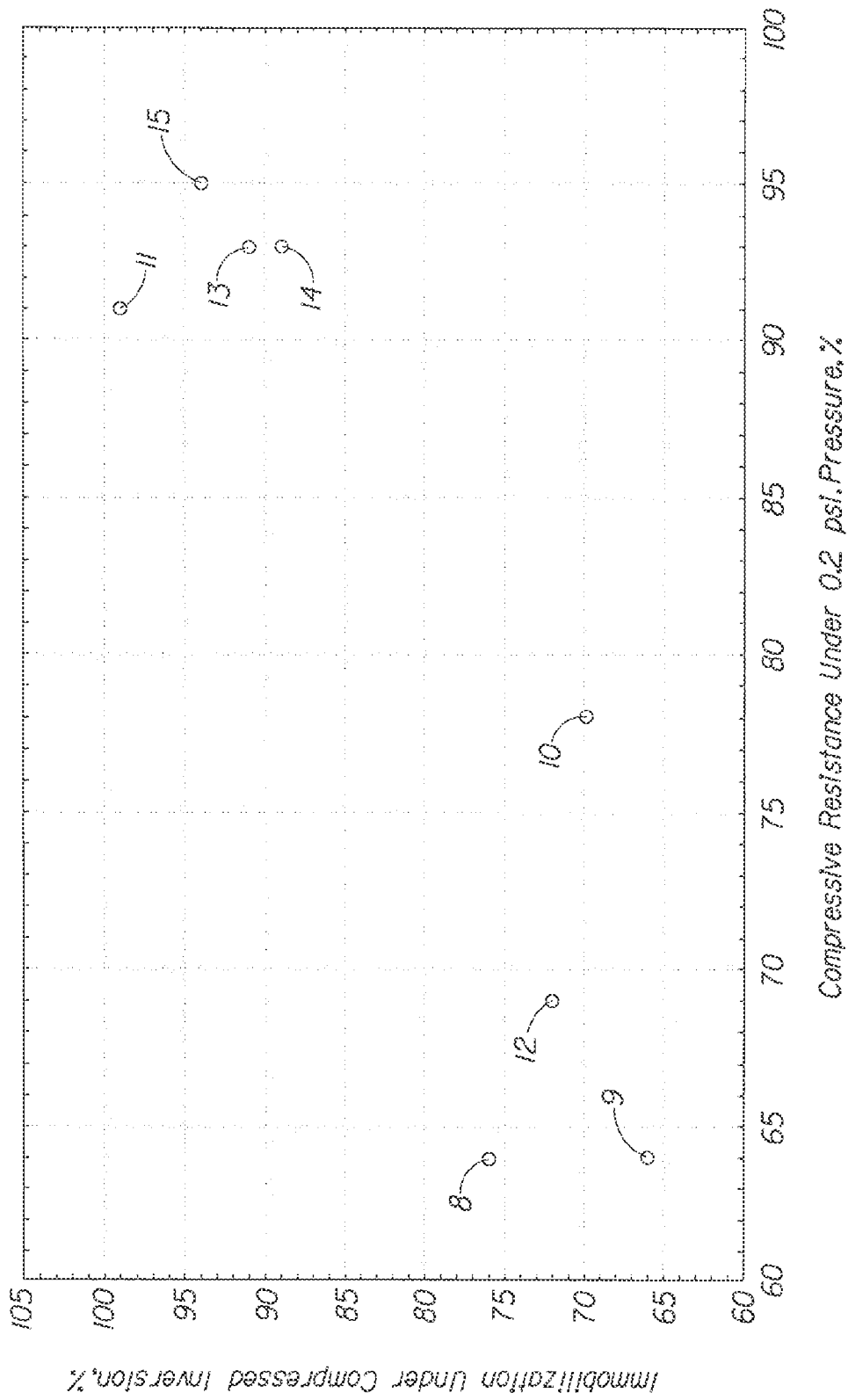
FIG. 16 is a 2-dimensional graphical representation of the relationship between Immobilization Under Compressed Inversion and Compressive Resistance values of exemplary structures.
Figure 17:
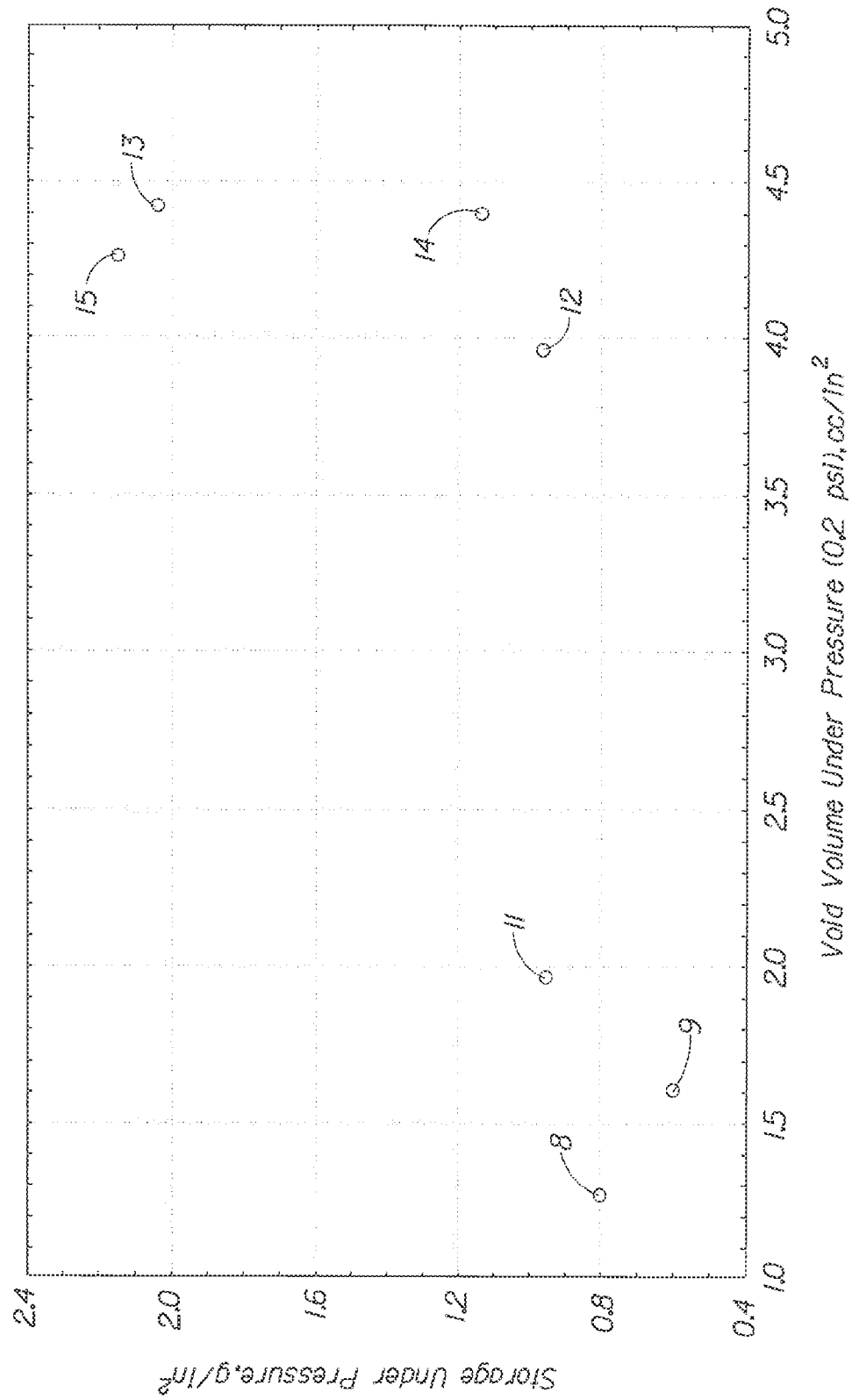
FIG. 17 is a 2-dimensional graphical representation of the relationship between Storage Under Pressure and Void Volume values of exemplary structures.
Figure 18:
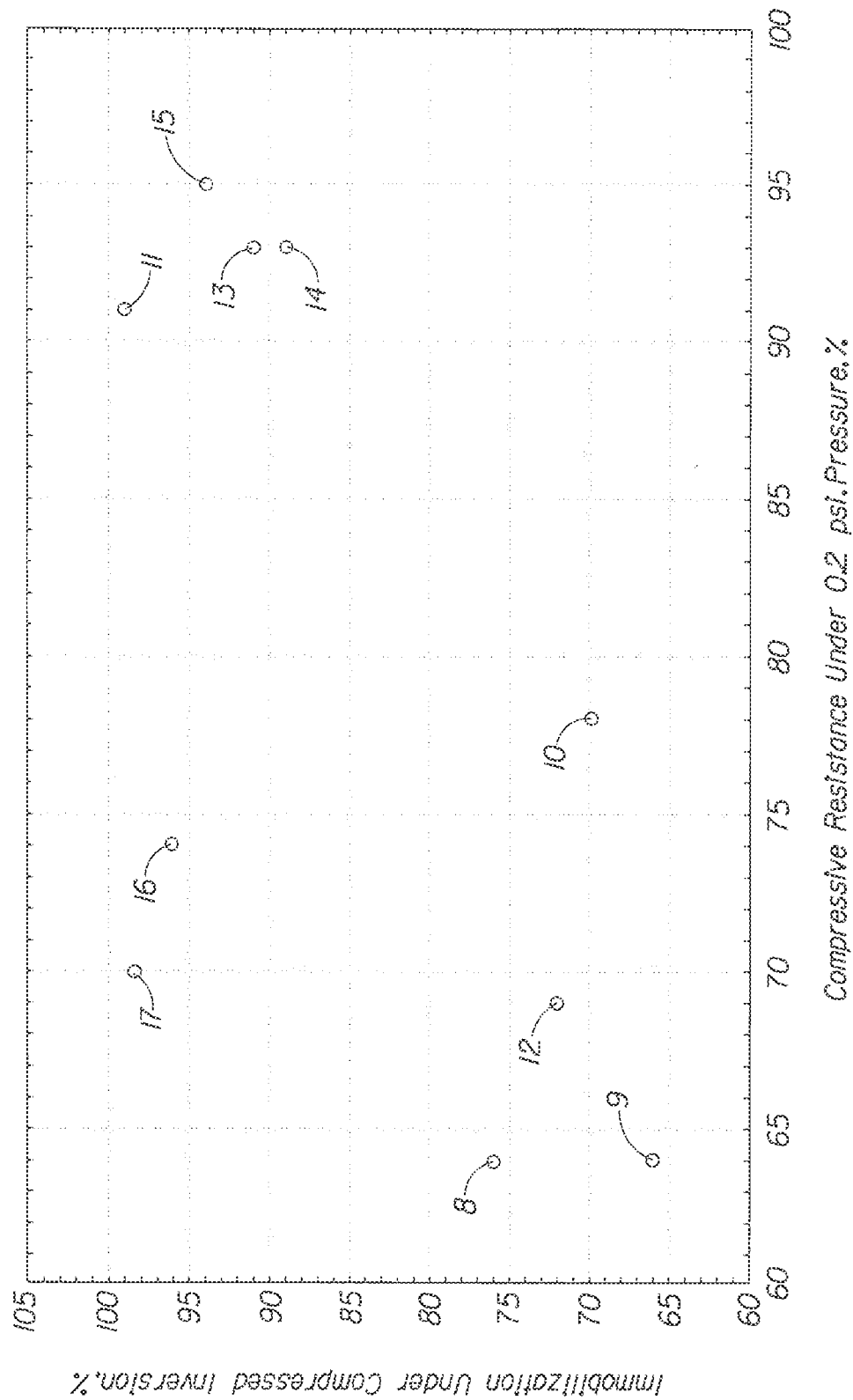
FIG. 18 is a 2-dimensional graphical representation of the relationship between Immobilization Under Compressed Inversion and Compressive Resistance values of exemplary structures.

The importance of the compressive resistance and void volume of the storage element is readily apparent in the graphs depicted in FIGS. 15, 16 and 17. The structures having higher compressive resistance and void volume clearly have significantly higher performance in terms of storage (FIGS. 15 and 17) and immobilization (FIG. 16). The improved performance due to increased compressive resistance can also make possible thinner, reduced caliper articles. Said another way, the caliper of the article may be reduced as compressive resistance increases because the void volume necessary to store and contain the waste can be maintained under normal in-use loads.

Examples 16 and 17 of the present invention provide excellent immobilization with compressive resistance less than 80. The improved immobilization is attained by the use of capillary channel fibers formed into loops (e.g. Example 16) and a reticulated foam placed over a loop material (e.g. Example 17). In such embodiments, the structural elements and combinations of elements provide immobilization which is clearly distinct from other articles with similar compressive resistance values. Alternative embodiments including similar or equivalent structures providing the improved performance of those described in Examples 16 and 17 are considered within the scope of the present invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article for wearing on or about a lower torso of a wearer for receiving bodily exudates, the disposable absorbent article comprising:
   a topsheet;
   a backsheet;
   an absorbent core disposed between at least a portion of the topsheet and the backsheet;
   an acceptance element having an effective open area of at least about 30% and an Acceptance Under Pressure value of greater than about 0.70 grams of a viscous fluid bodily waste per square inch of the acceptance element per milliJoule of energy input; and
   a storage element disposed between at least a portion of the acceptance element and the backsheet, the storage element having a compressive resistance of at least about 70%, and a Storage Under Pressure value of greater than about 0.70 grams of the viscous fluid bodily waste per square inch of the storage element.

2. The disposable absorbent article of claim 1, wherein the acceptance element has an Acceptance Under Pressure value of greater than about 1.0 grams of a viscous fluid bodily waste per square inch of the acceptance element per milliJoule of energy input.

3. The disposable absorbent article of claim 1, wherein the acceptance element has an Acceptance Under Pressure value of between about 0.8 and 10.0 grams of a viscous fluid bodily waste per square inch of the acceptance element per milliJoule of energy input.

4. The disposable absorbent article of claim 1, wherein the acceptance element has an effective open area of at least about 50%.

5. The disposable absorbent article of claim 1, wherein the acceptance element has an effective open area of between about 30% and 70%.

6. The disposable absorbent article of claim 1, wherein the acceptance element has apertures having an effective aperture size of at least about 0.2 square millimeters.

7. The disposable absorbent article of claim 1, wherein the acceptance element has apertures having an effective aperture size of at least about 1.0 square millimeters.

8. The disposable absorbent article of claim 1, wherein the acceptance element has apertures having an effective aperture size of at least about 2.0 square millimeters.

9. The disposable absorbent article of claim 1, wherein the topsheet is selected from the group consisting of: a porous foam, a reticulated foam, an apertured plastic film, a woven web of natural fibers, a nonwoven web of synthetic fibers, a woven web comprising natural and synthetic fibers, and a nonwoven web comprising natural and synthetic fibers.

10. The disposable absorbent article of claim 1, wherein the storage element has a Storage Under Pressure value of greater than about 1.0 grams of the viscous fluid bodily waste per square inch of the storage element.

11. The disposable absorbent article of claim 1, wherein the storage element has a Storage Under Pressure value of between at least about 0.8 and 10.0 grams of the viscous fluid bodily waste per square inch of the storage element.

12. The disposable absorbent article of claim 1, wherein the storage element has a compressive resistance of at least about 90%.

13. The disposable absorbent article of claim 1, wherein the storage element has a compressive resistance of between about 70% and 95%.

14. The disposable absorbent article of claim 1, wherein the storage element has a resiliency of at least about 80%.

15. The disposable absorbent article of claim 1, wherein the acceptance element is disposed between at least a portion of the topsheet and a portion of the storage element.

* * * * *